(12) United States Patent
Frankel et al.

(10) Patent No.: US 6,504,020 B1
(45) Date of Patent: Jan. 7, 2003

(54) ISOLATED NUCLEIC ACIDS COMPRISING LISTERIA DAL AND DAT GENES

(75) Inventors: Fred R. Frankel, Philadelphia, PA (US); Daniel A. Portnoy, Albany, CA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/520,207

(22) Filed: Mar. 7, 2000

Related U.S. Application Data

(62) Division of application No. 08/972,902, filed on Nov. 18, 1997, now Pat. No. 6,099,848.

(51) Int. Cl.$^7$ ............................................... C07H 21/04
(52) U.S. Cl. ..................................................... 536/23.1
(58) Field of Search ........................................ 536/23.1

(56) References Cited

FOREIGN PATENT DOCUMENTS

FR        WO 93/15212        8/1993

OTHER PUBLICATIONS

Lobocka et al. Organization and expression of the *Escherichia coli* K-12 dad operon encoding the smaller subunit of d-amino acid dehydrogenase and the catabolic alanine racemase. J. Bacteriol. vol. 176(5):1500–1510, Mar. 1994.*
Alexander, J.E. et al., "Characterization of an Aromatic Amino Acid—Dependent Listerial Monocytogenes Mutant: Attenuation, Persistence, and Ability To Induce Protective Immunity in Mice", Infection and Immunity, vol. 61, No. 5, 1993, pp. 2245–2248.
Marquis et al., "Intracytoplasmic Growth and Virulence of Listeria Monocytogenes Auxotrophic Mutants", Infection and Immunity, vol. 61, No. 9, 1993, pp. 3756–3760.
Tanaka, H., "DNA Sequence Coding D–Amino Acid Transaminase", Oct. 7, 1997, Database EMBL.
Ogasawara, N., "Bacillus Subtilis Genome Sequence", Oct. 13, 1997, Database EMBL.
Thompson, R.J. et al., "Pathogenicity and Immunogenicity of a *Listeria monocytogenes* Strain That Requires D–Alanine for Growth", Infection and Immunity, vol. 66, No. 8, 1998, pp. 3552–3561.
Bouwer et al., 1996, Infect.Immun. 64:2515–2522.
Brett et al., 1993, J.Immunol. 150:2869–2884.
Camilli et al., 1993, Mol. Microbiol. 8:143–157.
Collins et al., 1984, Proc. Natl. Acad. Sci. USA 81:6812–6816.
Coynault et al., 1996, Mol. Microbiol. 22:149–160.
Ferrari et al., 1985, Bio/technology 3:1003–1007.
Fouts et al., 1995, Vaccine 13:1697–1705.
Frankel et al., 1995, J. Immunol. 155:4775–4782.
Galakatos et al., 1986, Biochemistry 25:3255–3260.
Goossens et al., 1995, Int. Immunol. 7:797–802.
Harty et al., 1992, J. Exp. Med. 175:1531–1538.
Ikonomidis et al., 1997, Vaccine 15:433–440.
Innis et al., ed., 1990, In: PCR Protocols, Academic Press, Inc., San Diego—too voluminous to submit.
Kaufmann, 1993, Ann. Rev. Immunol. 11:129–163.
Noriega et al., 1996, Infect. Immun. 64:3055–3061.
Pamer et al., 1991, Nature 353:852–855.
Pan et al., 1995, Nat. Med. 1:471–477.
Paterson et al., 1996, Curr. Opin. Immunol. 8:664–669.
Portnoy et al. 1992, Infect. and Immun. 60:1263–1267.
Pucci et al., 1995, J. Bacteriol. 177:336–342.
Rubin et al., 1993, Proc. Natl. Acad. Sci. USA 90:9280–9284.
Sambrook, et al. 1989, In: Molecular Cloning: A Laboratory Manual, Cold Spring Harbor Laboratory, New York—(too voluminous to submit).
Schafer et al., 1992, J. Immunol. 149:53–59.
Shaw and Clewell, 1985, J. Bacteriol. 164:782–796.
Shen et al., 1995, Proc. Natl. Acad. Sci. USA 92:3987–3991.
Sizemore et al., 1995, Science 270:299–302.
Smith et al., 1992, Biochimie 74:705–711.
Tanizawa et al., 1989, J. Biol. Chem. 264:2450–2454.
Tanizawa et al., 1988, Biochemistry 27:1311–1316.
Tilney et al., 1989, J. Cell Biol. 109–1597–1608.
Triglia et al., 1988, Nucl. Acids Res. 16:8186.
Wasserman et al., 1984, Biochemistry 23:5182–5187.
Wipke et al., 1993, Eur. J. Immunol. 23:2005–2010.

* cited by examiner

*Primary Examiner*—Terry McKelvey
*Assistant Examiner*—William Sandals
(74) *Attorney, Agent, or Firm*—Morgan, Lewis & Bockius, LLP

(57) ABSTRACT

The invention includes auxotrophic attenuated mutants of Listeria and methods of their use as vaccines.

1 Claim, 17 Drawing Sheets

```
                              30
      *    *    *    *    *    *    *    *    *
    ATG  GTG  ACA  GGC  TGG  CAT  CGT  CCA  ACA  TGG  ATT  GAA  ATA  GAC  CGC  GCA
    Met  Val  Thr  Gly  Trp  His  Arg  Pro  Thr  Trp  Ile  Glu  Ile  Asp  Arg  Ala 60                                              90
      *    *    *    *    *    *    *    *    *    *
    GCA  ATT  CGC  GAA  AAT  ATA  AAA  AAT  GAA  CAA  AAT  AAA  CTC  CCG  GAA  AGT
    Ala  Ile  Arg  Glu  Asn  Ile  Lys  Asn  Glu  Gln  Asn  Lys  Leu  Pro  Glu  Ser

120
      *    *    *    *    *    *    *    *    *
    GTC  GAC  TTA  TGG  GCA  GTA  GTC  AAA  GCT  AAT  GCA  TAT  GGT  CAC  GGA  ATT
    Val  Asp  Leu  Trp  Ala  Val  Val  Lys  Ala  Asn  Ala  Tyr  Gly  His  Gly  Ile 150                                         180
      *    *    *    *    *    *    *    *    *    *
    ATC  GAA  GTT  GCT  AGG  ACG  GCG  AAA  GAA  GCT  GGA  GCA  AAA  GGT  TTC  TGC
    Ile  Glu  Val  Ala  Arg  Thr  Ala  Lys  Glu  Ala  Gly  Ala  Lys  Gly  Phe  Cys 210                                              240
      *    *    *    *    *    *    *    *    *    *
    GTA  GCC  ATT  TTA  GAT  GAG  GCA  CTG  GCT  CTT  AGA  GAA  GCT  GGA  TTT  CAA
    Val  Ala  Ile  Leu  Asp  Glu  Ala  Leu  Ala  Leu  Arg  Glu  Ala  Gly  Phe  Gln

270
      *    *    *    *    *    *    *    *    *
    GAT  GAC  TTT  ATT  CTT  GTG  CTT  GGT  GCA  ACC  AGA  AAA  GAA  GAT  GCT  AAT
    Asp  Asp  Phe  Ile  Leu  Val  Leu  Gly  Ala  Thr  Arg  Lys  Glu  Asp  Ala  Asn 300                                         330
      *    *    *    *    *    *    *    *    *    *
    CTG  GCA  GCC  AAA  AAC  CAC  ATT  TCA  CTT  ACT  GTT  TTT  AGA  GAA  GAT  TGG
    Leu  Ala  Ala  Lys  Asn  His  Ile  Ser  Leu  Thr  Val  Phe  Arg  Glu  Asp  Trp

360
      *    *    *    *    *    *    *    *    *
    CTA  GAG  AAT  CTA  ACG  CTA  GAA  GCA  ACA  CTT  CGA  ATT  CAT  TTA  AAA  GTA
    Leu  Glu  Asn  Leu  Thr  Leu  Glu  Ala  Thr  Leu  Arg  Ile  His  Leu  Lys  Val
```

Fig. 1A

```
          390                                         420
   *    *    *    *    *    *    *    *    *    *    *    *    *
  GAT  AGC  GGT  ATG  GGG  CGT  CTC  GGT  ATT  CGT  ACG  ACT  GAA  GAA  GCA  CGG
  Asp  Ser  Gly  Met  Gly  Arg  Leu  Gly  Ile  Arg  Thr  Thr  Glu  Glu  Ala  Arg 450                                              480
   *    *    *    *    *    *    *    *    *    *    *    *    *    *
  CGA  ATT  GAA  GCA  ACC  AGT  ACT  AAT  GAT  CAC  CAA  TTA  CAA  CTG  GAA  GGT
  Arg  Ile  Glu  Ala  Thr  Ser  Thr  Asn  Asp  His  Gln  Leu  Gln  Leu  Glu  Gly

510
            *    *    *    *    *    *    *    *    *
  ATT  TAC  ACG  CAT  TTT  GCA  ACA  GCC  GAC  CAG  CTA  GAA  ACT  AGT  TAT  TTT
  Ile  Tyr  Thr  His  Phe  Ala  Thr  Ala  Asp  Gln  Leu  Glu  Thr  Ser  Tyr  Phe 540                                         570
   *    *    *    *    *    *    *    *    *    *
  GAA  CAA  CAA  TTA  GCT  AAG  TTC  CAA  ACG  ATT  TTA  ACG  AGT  TTA  AAA  AAA
  Glu  Gln  Gln  Leu  Ala  Lys  Phe  Gln  Thr  Ile  Leu  Thr  Ser  Leu  Lys  Lys

600
       *    *    *    *    *    *    *    *    *
  CGA  CCA  ACT  TAT  GTT  CAT  ACA  GCC  AAT  TCA  GCT  GCT  TCA  TTG  TTA  CAG
  Arg  Pro  Thr  Tyr  Val  His  Thr  Ala  Asn  Ser  Ala  Ala  Ser  Leu  Leu  Gln 630                                         660
   *    *    *    *    *    *    *    *    *    *
  CCA  CAA  ATC  GGG  TTT  GAT  GCG  ATT  CGC  TTT  GGT  ATT  TCG  ATG  TAT  GGA
  Pro  Gln  Ile  Gly  Phe  Asp  Ala  Ile  Arg  Phe  Gly  Ile  Ser  Met  Tyr  Gly 690                                         720
   *    *    *    *    *    *    *    *    *    *
  TTA  ACT  CCC  TCC  ACA  GAA  ATC  AAA  ACT  AGC  TTG  CCG  TTT  GAG  CTT  AAA
  Leu  Thr  Pro  Ser  Thr  Glu  Ile  Lys  Thr  Ser  Leu  Pro  Phe  Glu  Leu  Lys

750
       *    *    *    *    *    *    *    *    *
  CCT  GCA  CTT  GCA  CTC  TAT  ACC  GAG  ATG  GTT  CAT  GTG  AAA  GAA  CTT  GCA
  Pro  Ala  Leu  Ala  Leu  Tyr  Thr  Glu  Met  Val  His  Val  Lys  Glu  Leu  Ala
```

Fig. 1B

```
                780                                              810
  *     *      *      *      *      *      *      *      *      *      *
 CCA   GGC    GAT    AGC    GTT    AGC    TAC    GGA    GCA    ACT    TAT    ACA    GCA    ACA    GAG    CGA
 Pro   Gly    Asp    Ser    Val    Ser    Tyr    Gly    Ala    Thr    Tyr    Thr    Ala    Thr    Glu    Arg

840
  *     *      *      *      *      *      *      *      *
 GAA   TGG    GTT    GCG    ACA    TTA    CCA    ATT    GGC    TAT    GCG    GAT    GGA    TTG    ATT    CGT
 Glu   Trp    Val    Ala    Thr    Leu    Pro    Ile    Gly    Tyr    Ala    Asp    Gly    Leu    Ile    Arg 870                                       900
  *     *      *      *      *      *      *      *      *      *
 CAT   TAC    AGT    GGT    TTC    CAT    GTT    TTA    GTA    GAC    GGT    GAA    CCA    GCT    CCA    ATC
 His   Tyr    Ser    Gly    Phe    His    Val    Leu    Val    Asp    Gly    Glu    Pro    Ala    Pro    Ile 930                                                     960
  *     *      *      *      *      *      *      *      *      *
 ATT   GGT    CGA    GTT    TGT    ATG    GAT    CAA    ACC    ATC    ATA    AAA    CTA    CCA    CGT    GAA
 Ile   Gly    Arg    Val    Cys    Met    Asp    Gln    Thr    Ile    Ile    Lys    Leu    Pro    Arg    Glu

990
  *     *      *      *      *      *      *      *      *
 TTT   CAA    ACT    GGT    TCA    AAA    GTA    ACG    ATA    ATT    GGC    AAA    GAT    CAT    GGT    AAC
 Phe   Gln    Thr    Gly    Ser    Lys    Val    Thr    Ile    Ile    Gly    Lys    Asp    His    Gly    Asn 1020                                              1050
  *     *      *      *      *      *      *      *      *      *
 ACG   GTA    ACA    GCA    GAT    GAT    GCC    GCT    CAA    TAT    TTA    GAT    ACA    ATT    AAT    TAT
 Thr   Val    Thr    Ala    Asp    Asp    Ala    Ala    Gln    Tyr    Leu    Asp    Thr    Ile    Asn    Tyr

1080
  *     *      *      *      *      *      *      *      *
 GAG   GTA    ACT    TGT    TTG    TTA    AAT    GAG    CGC    ATA    CCT    AGA    AAA    TAC    ATC    CAT
 Glu   Val    Thr    Cys    Leu    Leu    Asn    Glu    Arg    Ile    Pro    Arg    Lys    Tyr    Ile    His

*
 TAG
        *
```

Fig. 1C

```
LMDAL      1 .MVTGWHRPTWIEIDRAAIRENIKNEQNKLPES   32
BSTDAL     1 ..MNDFHRDTWAEVDLDAIYDNVENLRRLLPDD   31
BSUBDAL    1 MSTKPFYRDTWAEIDLSAIKENVSNMKKHIGEH   33

LMDAL     33 VDLWAVVKANAYGHGIIEVARTAKEAGAKGFCV   65
BSTDAL    32 THIMAVVKANAYGHGDVQVARTALERGPPP.AV   63
BSUBDAL   34 VHLMAVEKANAYGHGDAETAKAALDAGASCLAM   66

LMDAL     66 AILDEALALREAGFQDDFILVLGATRKEDANLA   98
BSTDAL    64 AFLDEALALREKGIEAP.ILVLGASRPADAALA   95
BSUBDAL   67 AILDEATSLRKKGLKAP.ILVLGAVPPEYVATA   98

LMDAL     99 AKNHISLTVFREDWLENL.TL.EA...TLRI..  124
BSTDAL    96 AQQRIALTVFRSDWLEEASALYSG...PFPIHF  125
BSUBDAL   99 AEYDVTLTGYSVEWLQEA.AR.HTKKGSL..HF  127

LMDAL    125 HLKVDSGMGRLGIRTTEEARRIEATSTNDHQLQ  157
BSTDAL   126 HLKMDTGMGRLGVKDEEETKRIVALIERHPHFV  158
BSUBDAL  128 HLKVDTGMNRLGVKTEEEVQNVMAILDRNPRLK  160

LMDAL    158 LEGIYTHFATADQLETSYFEQQLAKFQTILTSL  190
BSTDAL   159 LEGLYTHFATADEVNTDYFSYQYTRFLHMLEWL  191
BSUBDAL  161 CKGVFTHFATADEKERGYFLMQFERFKELIAPL  193

LMDAL    191 KKRPTYVHTANSAASL.LQPQIGFDAIRFGISM  222
BSTDAL   192 PSRPPLVHCANSAASLR.FPDRTFNMVRFGIAM  223
BSUBDAL  194 PLKNLMVHCANSAAGLRLKKGF.FNAVRFGIGM  225

LMDAL    223 YGLTPSTEIKTSLPFELKPALALYTEMVHVKEL  255
BSTDAL   224 YGLAPSPGIKPLLPYPLKEAFSLHSRLVHVKKL  256
BSUBDAL  226 YGLRPSADMSDEIPFQLRPAFTLHSTLSHVKLI  258

LMDAL    256 APGDSVSYGATYTATEREWVATLPIGYADGLIR  288
BSTDAL   257 QPGEKVSYGATYTAQTEEWIGTIPIGYADG.VR  288
BSUBDAL  259 RKGESVSYGAEYTAEKDTWIGTVPVGYADGWLR  291
```

Fig. 2A

```
LMDAL    289  HYSGFHVLVDGEPAPIIGRVCMDQTIIKLPREF  321
BSTDAL   289  RLQHFHVLVDGQKAPIVGRICMDQCMIRLPGPL  321
BSUBDAL  292  KLKGTDILVKGKRLKIAGRICMDQFMVELDQEY  324

LMDAL    322  QTGSKVTIIGKDHGNTVTADDAAQYLDTINYEV  354
BSTDAL   322  PVGTKVTLIGRQGDEVISIDDVARHLETINYEV  354
BSUBDAL  325  PPGTKVTLIGRQGDEYISMDEIAGRLETINYEV  357

LMDAL    355  TCLLNERIPRKYIH                    368
BSTDAL   355  PCTISYRVPRIFFRHKRIMEVRNAIGRGESSA  386
BSUBDAL  358  ACTISSRVPRMFLENGSIMEVRNPLLQVNISN  389
```

Fig. 2B

```
                                         30
           *        *    *        *       *    *        *        *    *
         ATG AAA GTA TTA GTA AAT AAC CAT TTA GTT GAA AGA GAA GAT GCC ACA
          M   K   V   L   V   N   N   H   L   V   E   R   E   D   A   T 60                                           90
           *        *    *        *        *    *        *        *    *    *
         GTT GAC ATT GAA GAC CGC GGA TAT CAG TTT GGT GAT GGT GTA TAT GAA
          V   D   I   E   D   R   G   Y   Q   F   G   D   G   V   Y   E

120
           *        *        *        *    *        *        *        *    *
         GTA GTT CGT CTA TAT AAT GGA AAA TTC TTT ACT TAT AAT GAA CAC ATT
          V   V   R   L   Y   N   G   K   F   F   T   Y   N   E   H   I 150                                        180
         *    *        *        *    *        *        *        *    *    *
         GAT CGC TTA TAT GCT AGT GCA GCA AAA ATT GAC TTA GTT ATT CCT TAT
          D   R   L   Y   A   S   A   A   K   I   D   L   V   I   P   Y 210                                    240
           *        *        *    *        *        *    *        *    *    *
         TCC AAA GAA GAG CTA CGT GAA TTA CTT GAA AAA TTA GTT GCC GAA AAT
          S   K   E   E   L   R   E   L   L   E   K   L   V   A   E   N

270
           *        *    *        *        *    *        *        *    *
         AAT ATC AAT ACA GGG AAT GTC TAT TTA CAA GTG ACT CGT GGT GTT CAA
          N   I   N   T   G   N   V   Y   L   Q   V   T   R   G   V   Q 300                                         330
         *    *        *        *    *        *        *        *    *    *
         AAC CCA CGT AAT CAT GTA ATC CCT GAT GAT TTC CCT CTA GAA GGC GTT
          N   P   R   N   H   V   I   P   D   D   F   P   L   E   G   V
```

Fig. 3A

```
                                360
     *     *     *     *     *     *     *     *     *
TTA ACA GCA GCA GCT CGT GAA GTA CCT AGA AAC GAG CGT CAA TTC GTT
 L   T   A   A   A   R   E   V   P   R   N   E   R   Q   F   V 390                                      420
 *     *     *     *     *     *     *     *     *     *
GAA GGT GGA ACG GCG ATT ACA GAA GAA GAT GTG CGC TGG TTA CGC TGT
 E   G   G   T   A   I   T   E   E   D   V   R   W   L   R   C 450                                            480
  *     *     *     *     *     *     *     *     *     *
GAT ATT AAG AGC TTA AAC CTT TTA GGA AAT ATT CTA GCA AAA AAT AAA
 D   I   K   S   L   N   L   L   G   N   I   L   A   K   N   K

510
  *     *     *     *     *     *     *     *     *
GCA CAT CAA CAA AAT GCT TTG GAA GCT ATT TTA CAT CGC GGG GAA CAA
 A   H   Q   Q   N   A   L   E   A   I   L   H   R   G   E   Q 540                                      570
  *     *     *     *     *     *     *     *     *     *
GTA ACA GAA TGT TCT GCT TCA AAC GTT TCT ATT ATT AAA GAT GGT GTA
 V   T   E   C   S   A   S   N   V   S   I   I   K   D   G   V

600
  *     *     *     *     *     *     *     *     *
TTA TGG ACG CAT GCG GCA GAT AAC TTA ATC TTA AAT GGT ATC ACT CGT
 L   W   T   H   A   A   D   N   L   I   L   N   G   I   T   R 630                                      660
 *     *     *     *     *     *     *     *     *     *
CAA GTT ATC ATT GAT GTT GCG AAA AAG AAT GGC ATT CCT GTT AAA GAA
 Q   V   I   I   D   V   A   K   K   N   G   I   P   V   K   E
```

Fig. 3B

```
                    690                                                    720
     *     *     *     *     *     *     *     *     *     *     *
   GCG   GAT   TTC   ACT   TTA   ACA   GAC   CTT   CGT   GAA   GCG   GAT   GAA   GTG   TTC   ATT
    A     D     F     T     L     T     D     L     R     E     A     D     E     V     F     I

750
            *     *     *     *     *     *     *     *     *     *
   TCA   AGT   ACA   ACT   ATT   GAA   ATT   ACA   CCT   ATT   ACG   CAT   ATT   GAC   GGA   GTT
    S     S     T     T     I     E     I     T     P     I     T     H     I     D     G     V 780                                                     810
      *    *     *     *     *     *     *     *     *     *
   CAA   GTA   GCT   GAC   GGA   AAA   CGT   GGA   CCA   ATT   ACA   GCG   CAA   CTT   CAT   CAA
    Q     V     A     D     G     K     R     G     P     I     T     A     Q     L     H     Q

840
         *    *     *     *     *     *     *     *     *
   TAT   TTT   GTA   GAA   GAA   ATC   ACT   CGT   GCA   TGT   GGC   GAA   TTA   GAG   TTT   GCA
    Y     F     V     E     E     I     T     R     A     C     G     E     L     E     F     A

870
    *     *
   AAA   TAA
    K     *
```

Fig. 3C

```
LMDAT     1   M.KVLVNNHLVEREDATVDIEDRGYQFGDGVYE   32
SHAEDAT   1   MTKVFINGEFIDQNEAKVSYEDRGYVFGDGIYE   33
BSPHDAT   1   MAYSLWNDQIVEEGSITISPEDRGYQFGDGIYE   33
BSPDAT    1   MGYTLWNDQIVKDEEVKIDKEDRGYQFGDGVYE   33

LMDAT    33   VVRLYNGKFFTYNEHIDRLYASAAKIDLVIPYS    65
SHAEDAT  34   YIRAYDGKLFTVTEHFERFIRSASEIQLDLGYT    66
BSPHDAT  34   VIKVYNGHMFTAQEHIDRFYASAEKIRLVIPYT    66
BSPDAT   34   VVKVYNGEMFTVNEHIDRLYASAEKIRITIPYT    66

LMDAT    66   KEELRELLEKLVAENNINTGNVYLQVTRGVQNP    98
SHAEDAT  67   VEELIDVVRELLKVNNIQNGGIYIQATRGV.AP    98
BSPHDAT  67   KDVLHKLLHDLIEKNNLNTGHVYFQITRGT.TS    98
BSPDAT   67   KDKFHQLLHELVEKNELNTGHIYFQVTRGT.SP    98

LMDAT    99   RNHVIPDDFPLEGVLTAAAREVPRNERQFVEGG   131
SHAEDAT  99   RNHSFPT.PEVKPVIMAFAKSYDRPYDDLENGI   130
BSPHDAT  99   RNHIFPD.ASVPAVLTGNVKTGERSIENFEKGV   130
BSPDAT   99   RAHQFPEN.TVKPVIIGYTKENPRPLENLEKGV   130

LMDAT   132   TAITEEDVRWLRCDIKSLNLLGNILAKNKAHQQ   164
SHAEDAT 131   NAATVEDIRWLRCDIKSLNLLGNVLAKEYAVKY   163
BSPHDAT 131   KATLVEDVRWLRCDIKSLNLLGAVLAKQEASEK   163
BSPDAT  131   KATFVEDIRWLRCDIKSLNLLGAVLAKQEAHEK   163

LMDAT   165   NALEAILHRGEQVTECSASNVSIIKDGVLWTHA   197
SHAEDAT 164   NAGEAIQHRGETVTEGASSNVYAIKDGAIYTHP   196
BSPHDAT 164   GCYEAILHRGDIITECSSANVYGIKDGKLYTHP   196
BSPDAT  164   GCYEAILHRNNTVTEGSSSNVFGIKDGILYTHP   196

LMDAT   198   ADNLILNGITRQVIIDVAKKNGIPVKEADFTLT   230
SHAEDAT 197   VNNYILNGITRKVIKWISEDEDIPFKEETFTVE   229
BSPHDAT 197   ANNYILNGITRQVILKCAAEINLPVIEEPMTKG   229
BSPDAT  197   ANNMILKGITRDVVIACANEINMPVKEIPFTTH   229
```

Fig. 4A

```
LMDAT    231  DLREADEVFISSTTIEITPLTHIDGVQVADGKR  263
SHAEDAT  230  FLKNADEVIVSSTSAEVTPVVKIDGEQVGDGKV  262
BSPHDAT  230  DLLTMDEIIVSSVSSEVTPVIDVDGQQIGAGVP  262
BSPDAT   230  EALKMDELFVTSTTSEITPVIEIDGKLIRDGKV  262

LMDAT    264  GPITAQLHQYFVEEITRACGELEFAK         289
SHAEDAT  263  GPVTRQLQEGFNKYIESRSS               282
BSPHDAT  263  GEWTRKLQKAFEAKLPISINA              283
BSPDAT   263  GEWTRKLQKQFETKIPKPLHI              283
```

Fig. 4B

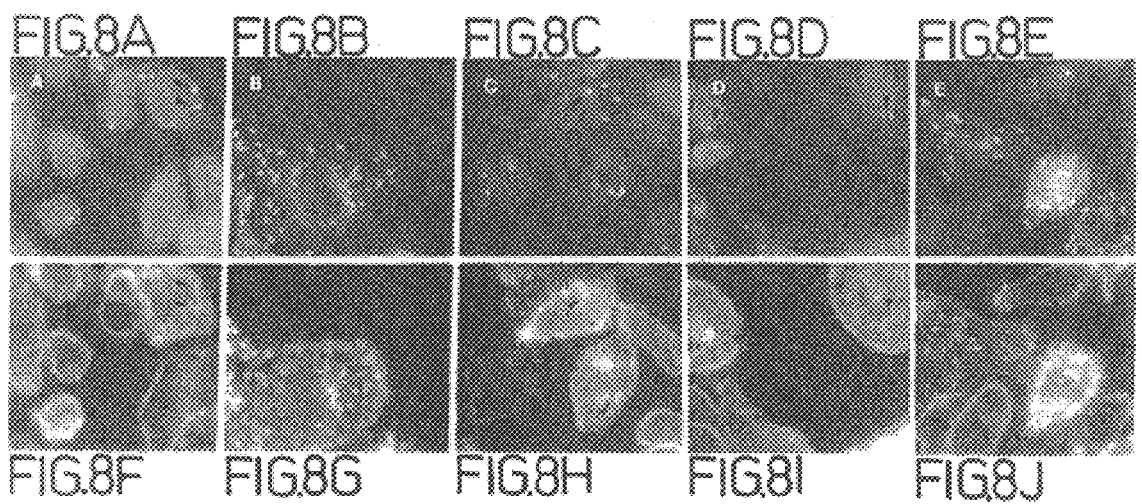

ISOLATED NUCLEIC ACIDS COMPRISING LISTERIA DAL AND DAT GENES

CROSS REFERENCE TO RELATED APPLICATIONS

This application is a divisional of U.S. application Ser. No. 08/972,902, filed on Nov. 18, 1997, now U.S. Pat. No. 6,099,848.

GOVERNMENT SUPPORT

This invention was supported in part by funds from the U.S. Government (NIH Grant Nos. AI-26919 and AI-27655) and the U.S. Government may therefore have certain rights in the invention.

FIELD OF THE INVENTION

The invention relates to vaccine vectors comprising bacteria.

BACKGROUND OF THE INVENTION

The use of vaccines is a cost-effective medical tool for the management of infectious diseases, including infectious diseases caused by bacteria, viruses, parasites, and fungi. In addition to effecting protection against infectious diseases, vaccines may now also be developed which stimulate the host's immune system to intervene in tumor growth.

Host immune responses include both the humoral immune response involving antibody production and the cell-mediated immune response. Protective immunization via vaccine has usually been designed to induce the formation of humoral antibodies directed against infectious agents, tumor cells, or the action of toxins. However, the control of certain diseases characterized by the presence of tumor cells or by chronic infection of cells with infectious agents, often requires a cell-mediated immune response either in place of, or in addition to the generation of antibody. While the humoral immune response may be induced using live infectious agents and agents which have been inactivated, a cellular immune response is most effectively induced through the use of live agents as vaccines. Such live agents include live infectious agents which may gain access to the cytoplasm of host cells where the proteins encoded by these agents are processed into epitopes which when presented to the cellular immune system, induce a protective response.

Microorganisms, particularly Salmonella and Shigella which have been attenuated using a variety of mechanisms, have been examined for their ability to encode and express heterologous antigens (Coynault et al., 1996, Mol. Microbiol. 22:149–160; Noriega et al., 1996, Infect. Immun. 64:3055–3061; Brett et al., 1993, J. Immunol. 150:2869–2884; Fouts et al., 1995, Vaccine 13:1697–1705, Sizemore et al., 1995, Science 270:299–302). Such bacteria may be useful as live attenuated bacterial vaccines which serve to induce a cellular immune response directed against a desired heterologous antigen.

*Listeria monocytogenes* (*L. monocytogenes*) is the prototypic intracellular bacterial pathogen which elicits a predominantly cellular immune response when inoculated into an animal (Kaufmann, 1993, Ann. Rev. Immunol. 11:129–163). When used as a vector for the transmission of genes encoding heterologous antigens derived from infectious agents or derived from tumor cells, recombinant Listeria encoding and expressing an appropriate heterologous antigen have been shown to successfully protect mice against challenge by lymphocytic choriomeningitis virus (Shen et al., 1995, Proc. Natl. Acad. Sci. USA 92:3987–3991; Goossens et al., 1995, Int. Immunol. 7:797–802) and influenza virus (Ikonomidis et al., 1997, Vaccine 15:433–440). Further, heterologous antigen expressing recombinant Listeria have been used to protect mice against lethal tumor cell challenge (Pan et al., 1995, Nat. Med. 1:471–477; Paterson and Ikonomidis, 1996, Curr. Opin. Immunol. 8:664–669). In addition, it is known that a strong cell-mediated immune response directed against HIV-1 gag protein may be induced in mice infected with a recombinant *L. monocytogenes* comprising HIV-1 gag (Frankel et al., 1995, J. Immunol. 155:4775–4782).

Although the potential broad use of Listeria as a vaccine vector for the prevention and treatment of infectious disease and cancer has significant advantages over other vaccines, the issue of safety during use of Listeria is not trivial. The use of the most common strain of Listeria, *L. monocytogenes*, is accompanied by potentially severe side effects, including the development of listeriosis in the inoculated animal. This disease, which is normally food-borne, is characterized by meningitis, septicemia, abortion and often a high rate of mortality in infected individuals. While natural infections by *L. monocytogenes* are fairly rare and may be readily controlled by a number of antibiotics, the organism may nevertheless be a serious threat in immunocompromised or pregnant patients. One large group individuals that might benefit from the use of *L. monocytogenes* as a vaccine vector are individuals who are infected with HIV. However, because these individuals are severely immunocompromised as a result of their infection, the use of *L. monocytogenes* as a vaccine vector is undesirable unless the bacteria are fully and irreversibly attenuated.

There is a need for the development of a strain of *L. monocytogenes* for use as a vaccine in and of itself and for use as a bacterial vaccine vector which is attenuated to the extent that it is unable to cause disease in an individual into whom it is inoculated. The present invention satisfies this need.

SUMMARY OF THE INVENTION

The invention includes a method of eliciting a T cell immune response to an antigen in a mammal comprising administering to the mammal an auxotrophic attenuated strain of Listeria which expresses the antigen, wherein the auxotrophic attenuated strain comprises a mutation in at least one gene whose protein product is essential for growth of the Listeria. In a preferred embodiment, the Listeria is *L. monocytogenes*. In another preferred embodiment, the auxotrophic attenuated strain is auxotrophic for the synthesis of D-alanine. In addition, the mutation comprises a mutation in both the dal and the dat genes of the Listeria.

In one aspect of the invention, the auxotrophic attenuated strain further comprises DNA encoding a heterologous antigen, or the the auxotrophic attenuated strain further comprises a vector comprising a DNA encoding a heterologous antigen.

The heterologous antigen may be an HIV-1 antigen.

The invention also includes a vaccine comprising an auxotrophic attenuated strain of Listeria which expresses an antigen, wherein the auxotrophic attenuated strain comprises a mutation in at least one gene whose protein product is essential for growth of the Listeria.

In preferred embodiments, the Listeria is *L. monocytogenes*. In other preferred embodiments, the auxotrophic attenuated strain is auxotrophic for the synthesis of D-alanine. In yet other preferred embodiments, the mutation comprises a mutation in both the dal and the dat genes of the Listeria.

The auxotrophic attenuated strain may further comprise DNA encoding a heterologous antigen or a vector comprising a DNA encoding a heterologous antigen.

The heterologous antigen may be an HIV-1 antigen.

Also included in the invention is an isolated nucleic acid sequence comprising a portion of a Listeria dal gene and an isolated nucleic acid sequence comprising a portion of a Listeria dat gene.

In addition, the invention includes an isolated strain of Listeria comprising a mutation in a dal gene and a mutation in a dat gene which render the strain auxotrophic for D-alanine. In one aspect, the isolated strain of Listeria further comprises a heterologous antigen.

BRIEF DESCRIPTION OF THE DRAWINGS

FIG. 1, comprising FIGS. 1A through 1C, is the DNA sequence of the *L. monocytogenes* alanine racemase gene (dal) of *L. monocytogenes* (SEQ ID NO:1) and the amino acid sequence encoded thereby (SEQ ID NO:2). The lysyl residue involved in the binding of pyridoxal-P is indicated by an asterisk.

FIG. 2, comprising FIGS. 2A and 2B, depicts the linear alignment of the deduced amino acid sequences of the alanine racemases of *L. monocytogenes* (LMDAL), (SEQ ID NO:2) *B. stearothermophilus*, (BSTDAL), (SEQ ID NO:3) and *B. subtilis (BSUBDAL) (SEQ ID NO:*4). Identical amino acids are boxed.

FIG. 3, is comprising FIGS. 3A through 3C, is the DNA sequence of the *L. monocytogenes* D-amino acid aminotransferase gene (dat) (SEQ ID NO:5) and the amino acid sequence encoded thereby (SEQ ID NO:6). The lysyl residue involved in the binding of pyridoxal-P is indicated by an asterisk.

FIG. 4, comprising FIGS. 4A and 4B, depicts the linear alignment of the deduced amino acid sequences of the D-amino acid aminotransferases of *L. monocytogenes* (LMDAT), (SEQ ID NO:5 ) *S. haemolyticus (SHAEDAT), (SEQ ID NO:7) B. sphaericus* (BSPHDAT), (SEQ ID NO:8) and Bacillus species YM-1 (BSPDAT)(SEQ ID NO:9). Identical amino acids are boxed.

FIG. 6, comprising FIG. 6C illustrates an infection by double mutant bacteria in the continuous presence of D-alanine (80 μg /ml). Arrowheads point to some mutant bacteria.

FIG. 7, comprising FIG. 7A also depicts mutant infection in the presence of D-alanine (100 μg/ml) (closed squares) and in the presence of D-alanine from 0 to 4 hrs during infection (open squares).

FIG. 8, comprising FIGS. 8A through 8J, is a series of images of photomicrographs depicting the association of actin with intracytoplasmic wild-type *L. monocytogenes* (FIGS. 8A and 8F: 2 hours; FIGS. 8B and 8G: 5 hours) or with the dal⁻dat⁻ double mutant of *L. monocytogenes* (FIGS. 8C and 8H: 2 hours wherein D-alanine was present from 0 to 30 minutes; FIGS. 8D and 8I: 5 hours, wherein D-alanine was present from 0 to 3 0 minutes; FIGS. 8E and 8J: 5 hours, wherein D-alanine was present continuously), following infection of J744 cells with these bacteria. The images on the top row illustrate the binding of FITC-labeled anti-Listerial antibodies to total bacteria (FIGS. 8A through 8E), while the bottom row illustrates the binding of TRITC-labeled phalloidin to actin (FIGS. 8F through 8J). The arrowheads point to some bacteria associated with actin.

FIG. 11, comprising FIG. 11B, dal⁻dat⁻ mutant: $3 \times 10^7$ bacteria (Δ); $3 \times 10^7$ bacteria with boost at 10 days (▲); $3 \times 10^7$ bacteria wherein animals were provided D-alanine subcutaneously (●○); $3 \times 10^7$ bacteria plus 2 mg/ml D-alanine ,(■) or 0.2 mg/ml D-alanine in drinking water (▲).

DETAILED DESCRIPTION OF THE INVENTION

Figure 5:
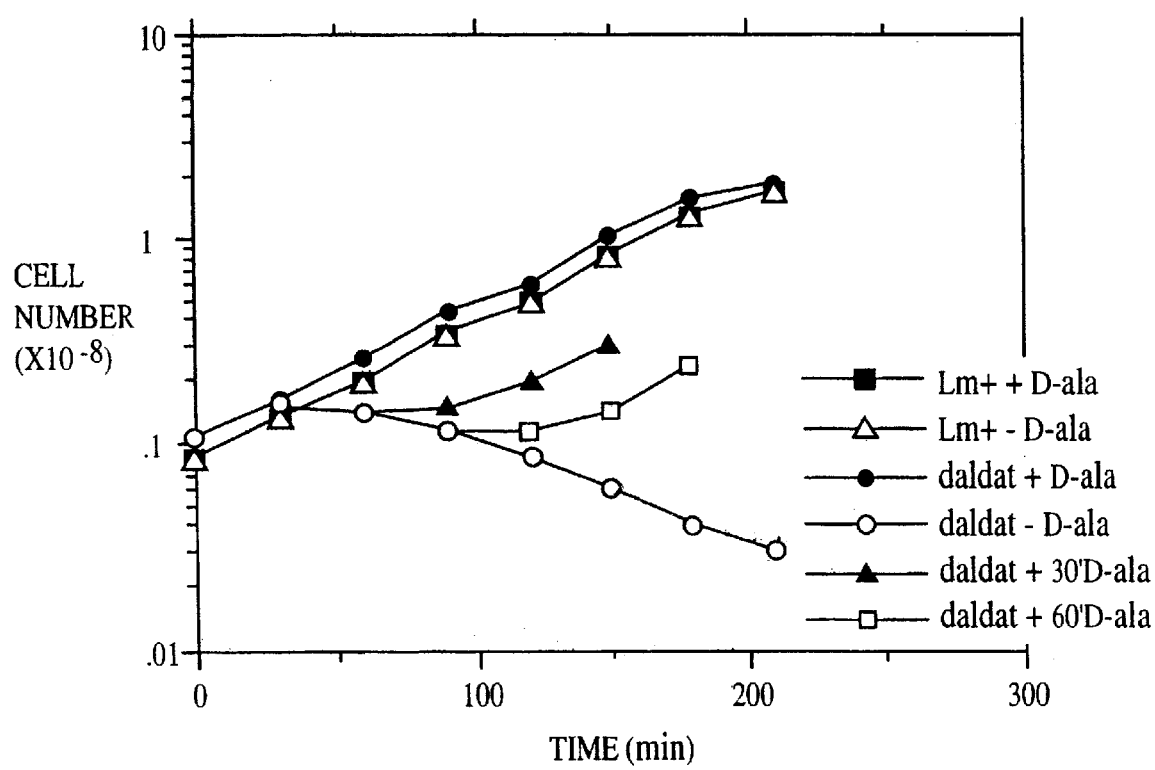
FIG. 5 is a graph depicting the growth requirement for D-alanine of the dal⁻dat⁻ double mutant strain of *L. monocytogenes*. The dal⁻dat⁻ (daldat) and wild-type (*L. monocytogenes*+) strains of *L. monocytogenes* were grown in liquid culture in BHI medium at 37° C. in the presence (+D-ala) or absence (−D-ala) of exogenous D-alanine (100 μg/ml). In additional experiments, the mutant cell culture was also provided D-alanine after 30 minutes and after 60 minutes.

The present invention relates to vaccines comprising attenuated strains of Listeria, wherein the bacteria have been attenuated by the introduction of auxotrophic mutations in the Listeria genomic DNA. These strains are herein referred to as attenuated auxotrophic strains or "AA strains" of Listeria.

It has been discovered in the present invention that the administration of an AA strain of Listeria to a mammal results in the development of a host cytotoxic T cell (CTL) response directed against Listeria following survival of the AA strain in the mammal for a time sufficient for the development of the response. The AA strain provides protection against challenge by *L. monocytogene* and is therefore suitable for use in a vaccine for protection against infection by this organism. The AA strain of the invention may thus be employed as a vaccine for the prevention and/or treatment of infection by Listeria. In addition, the AA strain of the invention may have added to it a heterologous gene wherein the gene is expressed by the AA strain. Such AA strains encoding additional heterologous genes are useful as bacterial vector vaccines for the prevention and/or treatment of infection caused by any number of infectious agents and for the prevention and/or treatment of tumors in mammals.

AA strains of Listeria that are auxotrophic for D-alanine are contemplated as part of this invention.

By the term "auxotrophic for D-alanine", as used herein, is meant that the AA strain of Listeria is unable to synthesize D-alanine in that it cannot grow in the absence of D-alanine and therefore requires exogenously added D-alanine for growth.

D-alanine is required for the synthesis of the peptidoglycan component of the cell wall of virtually all bacteria, and is found almost exclusively in the microbial world. Wild-type Listeria species synthesize D-alanine and thus do not require exogenously added D-alanine for growth. An AA strain of *L. monocytogenes* has been discovered in the present invention which is unable to synthesize D-alanine. This organism may be grown in the laboratory but is incapable of growth outside the laboratory in unsupplemented environments, including in the cytoplasm of eukaryotic host cells, the natural habitat of this organisms during infection. Such strains of Listeria are useful as vaccines.

By the term "vaccine," as used herein, is meant a population of bacteria which when inoculated into a mammal has the effect of stimulating a cellular immune response comprising a T cell response. The T cell response may be a cytotoxic T cell response directed against macromolecules produced by the bacteria. However, the induction of a T cell response comprising other types of T cells by the vaccine of the invention is also contemplated. For example, Listeria infection also induces both CD4+ T cells and CD8+ T cells. Induced CD4+ T cells are responsible for the synthesis of cytokines, such as interferon-γ, IL-2 and TNF-α. CD8+ T cells may be cytotoxic T cells and also secrete cytokines such as interferon-γ and TNF-α. All of these cells and the molecules synthesized therein play a role in the infection and subsequent protection of the host against Listeria. Cytokines produced by these cells activate additional T cells and also macrophages and recruit polymorphonuclear leukocytes to the site of infection.

Both prophylactic and therapeutic vaccines are contemplated as being within the scope of the present invention, that is, vaccines which are administered either prior to or subsequent to the onset of disease are included in the invention.

D-alanine auxotrophic mutants useful as vaccine vectors may be generated in a number of ways. As described in the Examples presented herein, disruption of one of the alanine racemase gene (dal) or the D-amino acid aminotransferase gene (dat), each of which is involved in D-alanine synthesis, did not result in a bacterial strain which required exogenously added D-alanine for growth. However, disruption of both the dal gene and the dat gene generated an AA strain of Listeria which required exogenously added D-alanine for growth.

The generation of AA strains of Listeria deficient in D-alanine synthesis may be accomplished in a number of ways that are well known to those of skill in the art, including deletion mutagenesis, insertion mutagenesis, and mutagenesis which results in the generation of frameshift mutations, mutations which effect premature termination of a protein, or mutation of regulatory sequences which affect gene expression. Mutagenesis can be accomplished using recombinant DNA techniques or using traditional mutagenesis technology using mutagenic chemicals or radiation and subsequent selection of mutants. Deletion mutants are preferred because of the accompanying low probability of reversion of the auxotrophic phenotype. Mutants of D-alanine which are generated according to the protocols presented herein may be tested for the ability to grow in the absence of D-alanine in a simple laboratory culture assay. Those mutants which are unable to grow in the absence of this compound are selected for further study.

In addition to the aforementioned D-alanine associated genes, other genes involved in D-alanine synthesis may be used as targets for mutagenesis of Listeria. Such genes include, but are not limited to any other known or heretofore unknown D-alanine associated genes.

Genes which are involved in the synthesis of other metabolic components in a bacterial cell may also be useful targets for the generation of attenuated auxotrophic mutants of Listeria, which mutants may also be capable of serving as bacterial vaccine vectors for use in the methods of the present invention. The generation and characterization of such other AA strains of Listeria may be accomplished in a manner similar to that described herein for the generation of D-alanine deficient AA strains of Listeria.

Additional potential useful targets for the generation of additional auxotrophic strains of Listeria include the genes involved in the synthesis of the cell wall component D-glutamic acid. To generate D-glutamic acid auxotrophic mutants, it is necessary to inactivate the dat gene, which is involved in the conversion of D-glu+ pyr to alpha-ketoglutarate + D-ala and the reverse reaction. It is also necessary to inactivate the glutamate racemase gene, dga. Other potential useful targets for the generation of additional auxotrophic strains of Listeria are the genes involved in the synthesis of diamimopimelic acid. In this instance, a gene encoding aspartate beta-semialdehyde dehydrogenase may be inactivated (Sizemore et al., 1995, Science 270:299–302).

By the term "attenuation," as used herein, is meant a diminution in the ability of the bacterium to cause disease in an animal. In other words, the pathogenic characteristics of the attenuated Listeria strain have been lessened compared with wild-type Listeria, although the attenuated Listeria is capable of growth and maintenance in culture. Using as an example the intravenous inoculation of Balb/c mice with an attenuated Listeria, the lethal dose at which 50% of inoculated animals survive ($LD_{50}$) is preferably increased above the $LD_{50}$ of wild-type Listeria by at least about 10-fold, more preferably by at least about 100-fold, more preferably at least about 1,000 fold, even more preferably at least about 10,000 fold, and most preferably at least about 100,000-fold. An attenuated strain of Listeria is thus one which does not kill an animal to which it is administered, or is one which kills the animal only when the number of bacteria administered is vastly greater than the number of wild type non-attenuated bacteria which would be required to kill the same animal. An attenuated bacterium should also be construed to mean one which is incapable of replication in the general environment because the nutrient required for its growth is not present therein. Thus, the bacterium is limited to replication in a controlled environment wherein the required nutrient is provided. The attenuated strains of the present invention are therefore environmentally safe in that they are incapable of uncontrolled replication.

It is believed that any Listeria species capable of infectious disease may be genetically attenuated according to the methods of the present invention to yield a useful and safe bacterial vaccine, provided the attenuated Listeria species exhibits an $LD_{50}$ in a host organism that is significantly greater than that of the non-attenuated wild type species. Thus, strains of Listeria other than *L. monocytogenes* may be used for the generation of attenuated mutants for use as vaccines. Preferably, the Listeria strain useful for the generation of attenuated vaccines is *L. monocytogenes*.

An AA strain of Listeria may be generated which encodes and expresses a heterologous antigen. The heterologous antigen encoded by the AA strain of Listeria is one which when expressed by Listeria is capable of providing protection in an animal against challenge by the infectious agent from which the heterologous antigen was derived, or which is capable of affecting tumor growth and metastasis in a manner which is of benefit to a host organism. Heterologous antigens which may be introduced into an AA strain of Listeria by way of DNA encoding the same thus include any antigen which when expressed by Listeria serves to elicit a cellular immune response which is of benefit to the host in which the response is induced. Heterologous antigens therefore include those specified by infectious agents, wherein an immune response directed against the antigen serves to prevent or treat disease caused by the agent. Such heterologous antigens include, but are not limited to, viral, bacterial, fungal or parasite surface proteins and any other proteins, glycoproteins, lipoprotein, glycolipids, and the like. Heterologous antigens also include those which provide benefit to a host organism which is at risk for acquiring or which is diagnosed as having a tumor. The host organism is preferably a mammal and most preferably, is a human.

By the term "heterologous antigen," as used herein, is meant a protein or peptide, a glycoprotein or glycopeptide, a lipoprotein or lipopeptide, or any other macromolecule which is not normally expressed in Listeria, which substantially corresponds to the same antigen in an infectious agent, a tumor cell or a tumor-related protein. The heterologous antigen is expressed by an AA strain of Listeria, and is processed and presented to cytotoxic T-cells upon infection of mammalian cells by the AA strain. The heterologous antigen expressed by Listeria species need not precisely match the corresponding unmodified antigen or protein in the tumor cell or infectious agent so long as it results in a T-cell response that recognizes the unmodified antigen or protein which is naturally expressed in the mammal.

By the term "tumor-related antigen," as used herein, is meant an antigen which affects tumor growth or metastasis in a host organism. The tumor-related antigen may be an antigen expressed by a tumor cell, or it may be an antigen which is expressed by a non-tumor cell, but which when so expressed, promotes the growth or metastasis of tumor cells.

The types of tumor antigens and tumor-related antigens which may be introduced into Listeria by way of incorporating DNA encoding the same, include any known or heretofore unknown tumor antigen.

The heterologous antigen useful in vaccine development may be selected using knowledge available to the skilled artisan, and many antigenic proteins which are expressed by tumor cells or which affect tumor growth or metastasis or which are expressed by infectious agents are currently known. For. example, viral antigens which may be considered as useful as heterologous antigens include but are not limited to the nucleoprotein (NP) of influenza virus and the gag protein of HIV. Other heterologous antigens include, but are not limited to, HIV env protein or its component parts gp120 and gp41, HIV nef protein, and the, HIV pol proteins, reverse transcriptase and protease. In addition, other viral antigens such as herpesvirus proteins may be useful. The heterologous antigens need not be limited to being of viral origin. Parasitic antigens, such as, for example, material antigens, are included, as are fungal antigens, bacterial antigens and tumor antigens.

As noted herein, a number of proteins expressed by tumor cells are also known and should be included in the list of heterologous antigens which may be inserted into the vaccine strain of the invention. These include, but are not limited to, the bcr/abl antigen in leukemia, HPVE6 and E7 antigens of the oncogenic virus associated with cervical cancer, the MAGE1 and MZ2-E antigens in or associated with melanoma, and the MVC-1 and HER-2 antigens in or associated with breast cancer.

The introduction of DNA encoding a heterologous antigen into a strain of Listeria may be accomplished, for example, by the creation of a recombinant Listeria in which DNA encoding the heterologous antigen is harbored on a vector, such as a plasmid for example, which plasmid is maintained and expressed in the Listeria species. Alternatively, DNA encoding the heterologous antigen may be stably integrated into the Listeria chromosome by employing, for example, transposon mutagenesis or by homologous recombination. A preferred method for producing recombinant Listeria having a gene encoding a heterologous antigen integrated into the chromosome thereof, is the induction of homologous recombination between a temperature sensitive plasmid comprising DNA encoding the antigen and Listeria chromosomal DNA. Stable transformants of Listeria which express the desired antigen may be isolated and characterized as described herein in the experimental examples. This method of homologous recombination is advantageous in that site directed insertion of DNA encoding the heterologous antigen is effected, thereby minimizing the possibility of disruption of other areas of the Listeria chromosome which may be essential for growth of this organism.

Several approaches may be employed to express the heterologous antigen in Listeria species as will be understood by one skilled in the art once armed with the present disclosure. Genes encoding heterologous antigens are preferably designed to either facilitate secretion of the heterologous antigen from the bacterium or to facilitate expression of the heterologous antigen on the Listeria cell surface.

While the heterologous antigen preferably comprises only a desired antigen along with appropriate signal sequences and the like, also contemplated in the invention is a fusion protein which comprises the desired heterologous antigen and a secreted or cell surface protein of Listeria. Listerial proteins which are suitable components of such fusion proteins include, but are not limited to, listeriolysin O (LLO) and phosphatidylinositol-specific phospholipase (PI-PLC). A fusion protein may be generated by ligating the genes which encode each of the components of the desired fusion protein, such that both genes are in frame with each other. Thus, expression of the ligated genes results in a protein comprising both the heterologous antigen and the listerial protein. Expression of the ligated genes may be placed under the transcriptional control of a listerial promoter/regulatory sequence such that expression of the gene is effected during growth and replication of the organism. Signal sequences for cell surface expression and/or secretion of the fused protein may also be added to genes encoding heterologous antigens in order to effect cell surface expression and/or secretion of the fused protein.

When the heterologous antigen is used alone (i.e., in the absence of fused Listeria sequences), it may be advantageous to fuse thereto signal sequences for cell surface expression and/or secretion of the heterologous antigen. The procedures for accomplishing this are well know in the art of bacteriology and molecular biology.

The DNA encoding the heterologous antigen which is expressed in the vaccine strain of the invention must be preceeded by a suitable promoter to facilitate such expression. The appropriate promoter/regulatory and signal sequences to be used will depend on the type of listerial protein desired in the fusion protein and will be readily apparent to those skilled in the art of listeria molecular biology. For example, preferred *L. monocytogenes* promoter/regulatory and/or signal sequences which may be used to direct expression of a fusion protein include, but are not limited to, sequences derived from the Listeria hly gene which encodes LLO, the Listeria p60 gene (Bouwer et al., 1996, Infect. Immun. 64:2515–2522) and possibly the Listeria actA gene which encodes a surface protein necessary for *L. monocytogenes* actin assembly. Other promoter sequences which might be useful in some circumstances include the picA gene which encodes Plc-PLC, the listeria mpl gene, which encodes a metalloprotease, the listeria plcB gene encoding a phospholipase C, and the listeria inlA gene which encodes internalin, a listeria membrane protein. For a review of genes involved in *L. monocytogenes* pathogenesis, see Portnoy et al. (1992, Infect. and Immun. 60:1263–267). It is also contemplated as part of this invention that heterologous regulatory elements such as promoters derived from phage and promoters or signal sequences derived from other bacterial species may be employed for the expression of a heterologous antigen by the Listeria species.

Examples of the use of recombinant *L. monocytogenes* strains that express a heterologous antigen for induction of an immnune response against tumor cell antigens or infectious agent antigens are described in U.S. patent application Nos. 08/366,372 and 08/366,477, now U.S. Pat. No. 5,830,702 respectively. The disclosures of these two patent applications are hereby incorporated herein by reference.

The data presented herein indicate that certain AA strains of Listeria may undergo osmotic lysis following infection of a host cell. Thus, if the Listeria which is introduced into the host cell comprises a vector, the vector is released into the cytoplasm of the host cell. The vector may comprise DNA encoding a heterologous antigen. Uptake into the nucleus of the vector DNA enables transcription of the DNA encoding the heterologous antigen and subsequent expression of the antigen in and/or secretion of the same from the infected host cell. Typically, the vector is a plasmid that is capable of replication in Listeria. The vector may encode a heterologous antigen, wherein expression of the antigen is under the control of eukaryotic promoter/regulatory sequences. Typical plasmids having suitable promoters that might be employed include, but are not limited to, pCMVbeta comprising the immediate early promoter/enhancer region of human cytomegalovirus, and those which include the SV40 early promoter region or the mouse mammary tumor virus LTR promoter region.

Thus, it is also contemplated as part of the present invention that AA strains of Listeria may be employed as a vaccine for the purpose of stimulating a CTL immune response against an infectious agent or a tumor cell, wherein the AA strain comprises a vector encoding a heterologous antigen that may be expressed using a eukaryotic expression system. According to the invention, the vector is propagated in the AA strain of Listeria concomitant with the propagation of the AA strain itself. The vector may be, for example, a plasmid that is capable of replication in the AA strain or the vector may be lysogenic phage. The vector must contain a prokaryotic origin of replication and must not contain a eukaryotic origin of replication in order that the vactor is capable of replication in a prokaryotic cell but, for safety reasons, is rendered absolutely incapable of replication in eukaryotic cells.

A cytotoxic T-cell response in a mammal is defined as the generation of cytotoxic T-cells capable of detectably lysing cells presenting an antigen against which the T cell response is directed. Preferably, within the context of the present invention, the T cell response is directed against a heterologous antigen expressed in an AA strain of Listeria or which is expressed by a vector which is delivered to a cell via Listeria infection. Assays for a cytotoxic T-cell response are well known in the art and include, for example, a chromium release assay (Frankel et al., 1995, J. Immunol. 155:4775–4782). In addition to a chromium release assay, an assay for released lactic acid dehydrogenase may be performed using a CYTOTOX 96 (non-radioactive cytotoxicity assay) kit obtained from Promega Biotech, WI.

In preferred embodiments and using a chromium release assay, at an effector cell to target cell ratio of about 50:1, the percentage of target cell lysis is preferably at least about 10% above the background level of cell lysis. The background level of cell lysis is the percent lysis of cells which do not express the target antigen. More preferably, the percentage of target cell lysis is at least about 20% above background; more preferably, at least about 40% above background; more preferably, at least about 60% above background; and most preferably, at least about 70% above background.

The vaccines of the present invention may be administered to a host vertebrate animal, preferably a mammal, and more preferably a human, either alone or in combination with a pharmaceutically acceptable carrier. The vaccine is administered in an amount effective to induce an immune response to the Listeria strain itself or to a heterologous antigen which the Listeria species has been modified to express. The amount of vaccine to be administered may be routinely determined by one of skill in the art when in possession of the present disclosure. A pharmaceutically acceptable carrier may include, but is not limited to, sterile distilled water, saline, phosphate buffered solutions or bicarbonate buffered solutions. The pharmaceutically acceptable carrier selected and the amount of carrier to be used will depend upon several factors including the mode of administration, the strain of Listeria and the age and disease state of the vaccinee. Administration of the vaccine may be by an oral route, or it may be parenteral, intranasal, intramuscular, intravascular, intrarectal, intraperitoneal, or any one of a variety of well-known routes of administration. The route of administration may be selected in accordance with the type of infectious agent or tumor to be treated. The vaccines of the present invention may be administered in the form of elixirs, capsules or suspensions for oral administration or in sterile liquids for parenteral or intravascular administration. The vaccine may also be administered in conjunction with a suitable adjuvant, which adjuvant will be readily apparent to the skilled artisan.

The immunogenicity of the AA strain of the invention may be enhanced in several ways. For example, a booster inoculation following the initial inoculation may be used to induce an enhanced CTL response directed against the AA strain.

In another approach, transient suppression of the auxotrophic phenotype of the AA strain is accomplished by providing the AA strain with the required nutrient for a period of time shortly before, after, or concomitant with administration of the Listeria vaccine to the host. The organism will replicate for the brief period during which the nutrient is present, after which, upon exhaustion of the supply of the nutrient, the organism will cease replication. This brief period of controlled replication will serve to provide more organisms in the host in a manner similar to that of natural infection by Listeria, which should stimulate an enhanced CTL response directed against the organism and antigens expressed thereby.

In yet another approach, the use of a suicide plasmid may be employed to conditionally suppress the attenuation of the Listeria AA strain by temporarily supplying the missing enzyme or enzymes to the bacterium for synthesis of the essential nutrient. A suitable suicide plasmid includes pKSV7, the same plasmid which was used to mediate insertion of genes into the Listeria chromosome as described herein. This plasmid contains a gram positive (for use in Listeria), temperature-sensitive replication system such that growth at 37–40° C. inhibits plasmid replication in Listeria. This plasmid also contains an $E.$ $coli$ replication system which is not temperature-sensitive (Smith et al., 1992, Biochimie 74:705–711). The plasmid, or even more temperature-sensitive derivatives thereof, may be further modified by inserting an alanine racemase gene into the plasmid, which modified plasmid is then inserted into an AA strain of Listeria. Listeria cells having the plasmid inserted therein, are replicated at 30° C. for a short period of time in order that some molecules of racemase are accumulated in the cytoplasm. The Listeria cells, so replicated are then injected into an animal or a human, wherein plasmid replication then ceases because of the temperature sensitive nature of the replication system at 37° C. Essentially, the cells would divide only a few times until the available racemase becomes diluted out, wherein the cells would cease replication altogether and become attenuated again. To ensure even tighter temperature sensitive replication, a temperature sensitive promoter may be used to regulate expression of the racemase gene and/or temperature sensitive mutations may be created in the racemase gene itself.

For treatment of cancer, the vaccine of the invention may be used to protect people at high risk for cancer. In addition, the vaccine may be used as an immunotherapeutic agent for the treatment of cancer following debulking of tumor growth by surgery, conventional chemotherapy, or radiation treatment. Patients receiving such treatment may be administered a vaccine which expresses a desired tumor antigen for the purpose of generating a CTL response against any residual tumor cells in the individual. The vaccine of the present invention may also be used to inhibit the growth of any previously established tumors in a human by either eliciting a CTL response directed against the tumor cells per se, or by eliciting a CTL response against cells which synthesize tumor promoting factors, wherein such a CTL response serves to kill those cells thereby diminishing or ablating the growth of the tumor.

The vaccine of the invention may be maintained in storage until use. Storage may comprise freezing the vaccine, or maintaining the vaccine at 4° C., room temperature, or the vaccine may first be lyophilized and then stored.

The invention particularly contemplates administration of a vaccine to a human for the purpose of preventing, alleviating, or ablating HIV infection. The protocol which is described herein for the administration of a vaccine to a human for the purpose of treating HIV infection is provided as an example of how to administer an attenuated auxotrophic Listeria strain as a vaccine to a human. This protocol should not be construed as being the only protocol which can be used, but rather, should be construed merely as an example of the same. Other protocols will become apparent to those skilled in the art when in possession of the present invention.

Essentially, an auxotrophic strain of $L.$ $monocytogenes$ which requires D-alanine for growth is constructed as described in the examples. The mutant is constructed by generating deletion mutations in both the dal gene and the dat gene, essentially following the procedures of Camilli et al., (1993, Mol. Microbiol. 8:143–157). The mutant strain is then modified using recombinant DNA techniques to express an HIV-1 antigen, preferably an antigenic portion of the gag protein, essentially as described in Frankel et al. (1995, J. Immunol. 155:4775–4778). A human is then immunized by injecting a solution containing the auxotrophic $L.$ $monocytogenes$ strain and a supplement of D-alanine.

One of ordinary skill in the art will know the quatities of cells and D-alanine which should be administered to the human based upon a knowledge of the dosages provided herein which are administered to mice. For example, in BALB/c mice, $10^7$ cells and 20 mg of D-alanine are the preferred dosages. Subsequent injections of the modified $L.$ $monocytogenes$ cells and D-alanine may also be given to boost the immune response.

Other HIV-1 antigens or proteins that may be used to generate a vaccine in accordance with this invention are the HIV env protein or its component parts, gp120 and gp 41, HIV gag, HIV nef and HIV pol or its component parts, reverse transcriptase and protease.

Isolated nucleic acid sequences encoding the dal gene and the dat gene of $L.$ $monocytogenes$ are also contemplated as part of this invention. In addition to their utility in generating deletion mutants of $L.$ $monocytogenes$ as disclosed herein, these isolated nucleic acid sequences encoding the dal gene and the dat gene may be used as probes and primers in identifying homologous genes in other Listeria species using PCR and other hybridization technology available in the art and described, for example, in Sambrook, et al. (1989, In: Molecular Cloning: A Laboratory Manual, Cold Spring Harbor Laboratory, New York; Innis et al., ed., 1990, In: PCR Protocols, Academic Press, Inc., San Diego). Additionally, the isolated nucleic acid sequences encoding dal or dat may be used to construct a suicide plasmid that expresses one or both of the genes. The suicide plasmid(s) may be used to complement the D-alanine Listeria auxotrophs for a limited time after immunization as disclosed herein.

An "isolated nucleic acid", as used herein, refers to a nucleic acid sequence, a DNA or an RNA or fragment thereof which has been separated from the sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g. RNA or DNA or proteins, which naturally accompany it in the cell. The term therefore includes, for example, a recombinant DNA which is incorporated into a vector; into an autonomously replicating plasmid or virus; or into the genomic DNA of a prokaryote or eukaryote; or which exists as a separate molecule (e.g, as a cDNA or a genomic or cDNA fragment produced by PCR amplification, restriction enzyme digestion or chemical synthesis) independent of other sequences. It also includes a recombinant DNA which is part of a hybrid gene encoding additional polypeptide sequence.

Typically probes and primers for use in identifying other dal and dat genes will comprise a portion of a Listeria dal or dat gene that is at least about 15 consecutive nucleotides. More typically, a probe or primer comprises a portion of at least about 20, even more typically, at least about 30 and even more typically, at least about 40 consecutive nucleotides of a dal or dat gene of Listeria.

In other related aspects, the invention includes a vectors which comprises an isolated nucleic acid encoding dal or dat and which is preferably capable, of directing expression of the protein encoded by the nucleic acid in a vector-containing cell. The invention further includes cells comprising a vector encoding dal or dat, including both prokaryotic and eukaryotic cells.

The isolated nucleic acids of the invention should be construed to include an RNA or a DNA sequence specifying the dal gene or the dat gene, and any modified forms thereof, including chemical modifications of the DNA or RNA which render the nucleotide sequence more stable when it is cell free or when it is associated with a cell. Chemical modifications of nucleotides may also be used to enhance the efficiency with which a nucleotide sequence is taken up by a cell or the efficiency with which it is expressed in a cell. Any and all combinations of modifications of the nucleotide sequences are contemplated in the present invention.

The invention should not be construed as being limited solely to the DNA and amino acid sequences shown in FIGS. 1 and 3. Once armed with the present invention, it is readily apparent to one skilled in the art that any other DNA and encoded amino acid sequence of the dal and dat genes of other Listeria species may be obtained by following the procedures described herein. The invention should therefore be construed to include any and all dal and dat DNA sequence and corresponding amino acid sequence, having substantial homology to the dal and dat DNA sequence, and the corresponding amino acid sequence, shown in FIGS. 1 and 3, respectively (SEQ ID NOS: 1,2,5, and 6 respectively). Preferably, DNA which is substantially homologous is about 50% homologous, more preferably about 70% homologous, even more preferably about 80% homologous and most preferably about 90% homologous to the dal or dat DNA sequence shown in FIGS. 1 and 3, respectively. Preferably, an amino acid sequence which is substantially homologous is about 50% homologous, more preferably about 70% homologous, even more preferably about 80% homologous and most preferably about 90% homologous to the amino acid sequences encoded by the dal and dat genes shown in FIGS. 1 and 3, respectively (SEQ ID NOS:1,2,5 and 6 respectively).

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGCG5' share 50% homology.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

The experimental examples described herein provide procedures and results which establish that attenuated auxotrophic mutants of *L. monocytogenes* are useful as vaccines for eliciting a CTL response.

Materials and Methods useful in the construction and use of an attenuated auxotrophic *L. monocytogenes* strain are now described.

Bacteria and Plasmids

The *L. monocytogenes* strain 10403S (Portnoy et al., 1988, supra) comprises the wild-type organism used in these studies. This organism was propagated in brain/heart infusion medium (BHI) (Difco Labs). *L. monocytogenes* strain 10403S has an $LD_{50}$ of approximately $3 \times 10^4$ when injected intravenously or intraperitoneally into BALB/c mice (Schafer et al., 1992, J. Immunol. 149:53–59).

*E. coli* DH5a was used for cloning. This organism was propagated in Luria broth (Sambrook et al., 1989, supra). The plasmid pKSV7, which was used for allelic exchange reactions in *L. monocytogenes*, is a shuttle vector capable of replication in *E. coli*, where it is selected in the presence of 50 µg of ampicillin per ml of media, and in *L. monocytogenes*, wherein replication of the plasmid is temperature sensitive and is selected in the presence of 10 µg of chloramphenicol per ml of media (Smith et al., 1992, Biochimie 74:705–711). Plasmid DNA obtained from *E. coli* and total DNA (chromosomal and plasmid) from obtained from *Listeria monocytogenes* were isolated using standard methods (Sambrook et al., 1989, supra).

Identification of D-alanine Synthesis Genes in *L. monocytogenes* by Homology with D-alanine Synthesis Genes in other Gram Positive Organisms Based on sequences of the alanine racemase gene (dal) in gram-positive organisms (Ferrari et al., 1985, Bio/technology 3:1003–1007; Tanizawa et al., 1988, Biochemistry 27:1311–1316), primers were designed which corresponded to two 20 base consensus sequences from highly conserved regions at the 5' and 3' ends of the dal gene. These primers were modified to reflect the preferred codon usage in Listeria. These primers were used in a PCR reaction using chromosomal DNA from either , *L. mononocytogenes* or *B. subtilis* as templates. A similar sized PCR product (850 nucleotides) was obtained from both *L. monocytogenes* and *B. subtilis*. Analysis of the 850 nucleotide PCR product from the Listeria template, and the amino acid sequence encoded thereby, indicated substantial homology with the alanine racemase genes of the other gram-positive organisms.

A similar strategy was used to identify and sequence a portion of a D-amino acid aminotransferase gene (dat) of Listeria, based on sequences in *B. sphaericus, B. species* YM-1 (Tanizawa et al., 1989, supra), and Pucci et al., 1995, J. Bacteriol. 177:336–342). Primers based on dat sequence in the other gram positive organisms was used for PCR amplification of *L. monocytogenes* DNA and a PCR product of about 400 nucleotides was obtained. Analysis of the DNA sequence of the 400 nucleotide PCR product, and the amino acid sequence encoded thereby, indicated substantial homology with the aminotransferase genes of the other gram positive organisms.

Strategy for Sequence Determination of the Complete Genes

The sequence of the remaining portions of the L. monocytogenes dal gene adjoined to the 5' and 3' ends of the central PCR product was determined using anchored PCR reactions (Rubin et al., 1993, Proc. Natl. Acad. Sci. USA 90:9280–9284). Briefly, this procedure utilized a BglII-restriction digest (for the 5' portion of the gene) or a XbaI digest (for the 3' portion of the gene) of Listeria chromosomal DNA. The ends of the digested Listeria chromosomal DNA were then ligated to a small fragment of DNA containing the T7 promoter. A 5'-portion PCR product and a 3'-portion PCR product were then made and sequenced using primers from within the central dal gene PCR product and a second primer homologous to the T7 promoter fragment. This procedure permitted determination of the entire sequence of the dal gene.

The sequence of the remainder of the dat gene was determined by use of an inverse PCR reaction (Collins et al., 1984, Proc. Natl. Acad. Sci. USA 81:6812–6816; Triglia et al., 1988, Nucl. Acids Res. 16:8186). Briefly, a HindIII digest of Listeria chromosomal DNA was permitted to self-ligate under conditions of low DNA concentration so that mainly single circular molecules would form. Outward-directing primers with homologies at the two ends of the original PCR segment of the gene were then used to make a new PCR product that began at the 5'-end of the original PCR segment, proceeded to the 5'-end of the gene through the HindIII self-ligation site and into the 3'-end of the gene. Using this method, the entire dat gene sequence was obtained.

Production of Mutations in Listeria dal and dat Genes

The dal gene was inactivated by means of a double allelic exchange reaction following the protocol of Camilli et al. (Camilli et al., 1993, Mol. Microbiol 8:143–157). A ts shuttle plasmid pKSV7 (Smith et al., 1992, supra) construct containing an erythromycin gene (Shaw and Clewell, 1985, J. Bacteriol. 164:782–796) situated between a 450-base pair fragment of the 5' end of the 850-base pair dal gene PCR product and a 450-base pair fragment of the 3' end of the dal gene PCR product was introduced into Listeria to produce a double allelic exchange reaction between the chromosomal dal gene and the plasmid pKSV7 dal construct. A dal deletion mutant covering about 25% of the gene in the region of its active site was obtained.

The chromosomal dat gene of L. monocytogenes was also inactivated using a double allelic exchange reaction. A pKSV7 plasmid construct containing 450-base pair fragments corresponding to the 5' and 3' ends of the dat gene PCR product, which had been joined together by an appropriate PCR reaction, was introduced into Listeria. A double allelic exchange reaction between the chromosomal dat gene and the dat plasmid construct resulted in the deletion of 30% of the central bases of the dat gene.

Infection of Cells in Culture

To examine the intracellular growth of the attenuated strain of Listeria in cell culture, monolayers of J774 cells, a murine macrophage-like cell line, primary murine bone marrow macrophages, and the human HeLa cell line, were grown on glass coverslips and infected as described (Portnoy et al., 1988, supra). To enhance the efficiency infection of HeLa cells, a naturally non-phagocytic cell line, the added bacteria were centrifuged onto the HeLa cells at 543×g for 15 minutes. At various times after infection, samples of the cultures were obtained in order to perform differential staining for the determination of viable intracellular bacteria, or for immunohistochemical analysis.

Immunohistochemistry

Coverslips with attached infected macrophages or HeLa cells were washed with PBS, and the cells were fixed in 3.2% formalin and permeabilized using 0.05% TWEEN (polyoxyethylene (20) sorbitan monolaurate) 20. Listeria were detected using rabbit anti-Listeria O antiserum (Difco Laboratories) followed by LSRSC-labeled donkey anti-rabbit antibodies or coumarin-labeled goat anti-rabbit antibodies. Actin was detected using FITC- or TRITC-labeled phalloidin. To distinguish extracellular (or phagosomal) from intracytoplasmic bacteria, the former were stained prior to permeabilization of the cells.

Induction of Listeriolysin O-specific CTLs

Female BALB/c mice, 6 to 8 weeks of age (Charles River Laboratories, Raleigh, N.C.) were immunized by intraperitoneal inoculation with either wild-type or dal$^-$dat$^-$ strains of L. monocytogenes. After 14 days, some of the mice were boosted with a second inoculation containing the same number of microorganisms as were given in the first inoculation. Ten or more days after the last inoculation, $6 \times 10^7$ splenocytes obtained from a given animal were incubated in Iscove's modified DMEM with $3 \times 10^7$ splenocytes from that same animal that had been loaded with 10 $\mu$M listeriolysin O (LLO) peptide 91–99 during a 60 minute incubation at 37° C. After five days of in vitro stimulation, the resulting cultures were assayed for the presence of CTL activity capable of recognizing LLO-peptide-labeled P815 cells following previously published procedures (Wipke et al., 1993, Eur. J. Immunol. 23:2005–2010; Frankel et al., 1995, supra). Every determination of lytic activity was corrected for activity in unlabeled target cells, which exhibited between 1 and 10 percent lysis.

Animal Protection Studies

Female BALB/c mice (Bantin-Klingman, Freemont, Calif. at 8 weeks of age were immunized with approximately 0.1 $LD_{50}$ of viable wild-type L. monocytogenes or the dal$^-$dat$^-$ double mutant strain in 0.2 ml of vehicle, by tail vein injection. Three to four weeks following immunization, groups of four to five mice each were challenged with approximately 10 $LD_{50}$ of viable wild-type L. monocytogenes strain 10403 in 0.2 ml of vehicle, by tail vein injection. Spleens were removed from the mice 48 hours later and were homogenized individually in 4.5 ml PBS-1% proteose-peptone using a tissue homogenizer (Tekmar). The homogenates were serially diluted and plated onto BHI agar. $Log_{10}$ protection was determined by subtracting the mean of the $log_{10}$ CFU/spleen values of the test group from the mean of the $log_{10}$ CFU/spleen values of the normal control group.

Construction of an Auxotrophic Attenuated Strain of L. monocytogenes Useful as a Vaccine Construction of an Attenuated Strain of *L. monocytogenes* Defective in Cell Wall Synthesis

*L. monocytogenes* was examined to determine whether the bacteria harbor genes for the synthesis of D-alanine. The alanine racemase (dal) gene, used by many microorganisms for the synthesis of D-alanine, has been sequenced in Salmonella (Galakatos et al., 1986, Biochemistry 25:3255–3260; Wasserman et al., 1984, Biochemistry 23:5182–5187), *B. subtilis* (Ferrari et al., 1985, Bio/technology 3:1003–1007), and *B. stearothermophilis* (Tanizawa et al., 1988, Biochemistry 27:1311–1316), but the gene has not been reported in Listeria. Primers based on the sequences (adjusted for preferred codon usage in Listeria) of two highly conserved regions of the dal gene in two different gram-positive organisms were employed in a PCR reaction performed on *L. monocytogenes* chromosomal DNA to search for evidence of the dal gene in Listeria. A product that exhibited significant homology with the published dal gene sequences was obtained. The sequence of the remainder of the *L. monocytogenes* dal gene was determined as described herein and is depicted in FIG. 1. The translated protein sequence is compared with alanine racemases of the other gram-positive organisms in FIG. 2.

The dal gene was inactivated by an in-frame insertion of a 1.35 kb fragment of DNA encoding erythromycin resistance at an SpeI site near the center of the gene. The resulting dal⁻ bacteria were found to grow both in rich bacteriological medium (BHI) as well as in a synthetic medium in the presence or absence of D-alanine. Mutation of the dal gene was also achieved by an in-frame deletion covering 82% of the gene with the same effect.

A second enzyme used by some bacteria for synthesis of D-alanine is D-amino acid aminotransferase, encoded by the dat gene (Tanizawa et al., 1989, J. Biol. Chem. 264:2450–2454; Pucci et al., 1995, J. Bacteriol. 177:336–342). Following the same strategy used to detect the dal gene in *L. monocytogenes*, a PCR product that exhibited significant sequence homology with known dat genes and gene products was obtained. The sequence obtained from the PCR product was only the partial gene sequence, and remainder of the dat gene gene sequence (as depicted in FIG. 3) was determined according to procedures described herein. The deduced protein sequence of the *L. monocytogenes* dat gene is compared with other dat gene products in FIG. 4.

The *L. monocytogenes* dat gene was inactivated by in-frame deletion of 31% of its central region. The growth of the resulting dal⁻ bacteria in various bacteriological media was again found to be independent of the presence of D-alanine.

A double mutant strain of *L. monocytogenes*, dal⁻dat⁻-1, was produced by a double allelic exchange reaction between the erythromycin-resistant dal⁻ organism and the shuttle vector carrying the dat gene deletion. The growth of the double mutant in bacteriological media was found to be completely dependent on the presence of D-alanine (FIG. 5). A double mutant containing deletions in both of the genes, designated dal⁻dat⁻-12, had the same phenotype. The growth of the double-deletion strain in the absence of D-alanine could be complemented by a plasmid carrying the dal gene of *B. subtillis*. All of the dal⁻dat⁻ double mutant experiments reported in the following examples employed the dat⁻ dat⁻-1 double mutant.

Expression of the Defective Phenotype Following Infection of Eukaryotic Cells

To determine whether a defect in the ability of *L. monocytogenes* to synthesize D-alanine would be expressed as an inability to replicate in the cytoplasm of eukaryotic cells because of the absence of the required D-alanine in the cytoplasm, several different cell lines and primary cells in culture were infected with the wild-type and mutant strains of this organism.

Figure 6A:
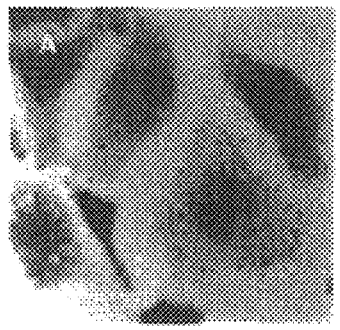
FIGS. 6A through 6C is a series of images of light micrographs depicting the growth of wild-type *L. monocytogenes* (FIG. 6A) and the dal⁻dat⁻ double mutant strain of *L. monocytogenes* (FIG. 6B) in J774 macrophages at 5 hours after infection with about 5 bacteria per mouse cell.
Figure 6B:
Figure 6C:
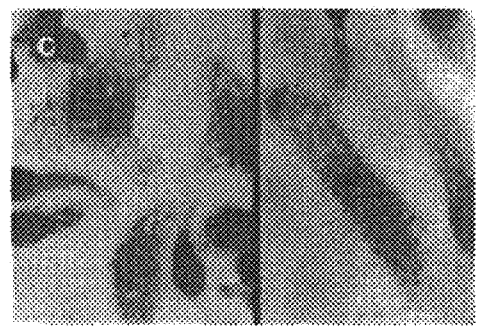

J774 cells are a mouse macrophage-like cell line that readily take up *L. monocytogenes* by phagocytosis and permit its cytoplasmic growth following escape of the bacteria from the phagolysosome (Tilney et al., 1989, J. Cell Biol. 109:1597–1608). FIG. 6 depicts typical J774 cells as observed at 5 hours after infection with about 5 bacteria per cell of either wild-type Listeria (Panel A) or the double dal⁻dat⁻ mutant Listeria (Panel B). Whereas large numbers of bacteria were observed to be associated with mouse cells infected with wild-type Listeria, few were seen following infection with the double mutant bacteria. Infection by double mutant bacteria in culture medium containing D-alainine permitted bacterial growth which was indistinguishable from that seen in cells infected with wild type Listeria (FIG. 6, Panel C).

Some J774 cells contained small round darkly-staining objects, often in pairs, that may be spheroblast-like bacteria, although they were not examined further. When these cells were infected at higher multiplicities (a multiplicity of infection of about 1–10), many cells contained multiple microorganisms, but the double mutant again failed to multiply. Most double mutant-infected cells possessed pychnotic nuclei and a pale cytoplasm and presumably were dead; mouse cells harboring wild-type Listeria did not exhibit this property at any time after infection.

Figure 7A:
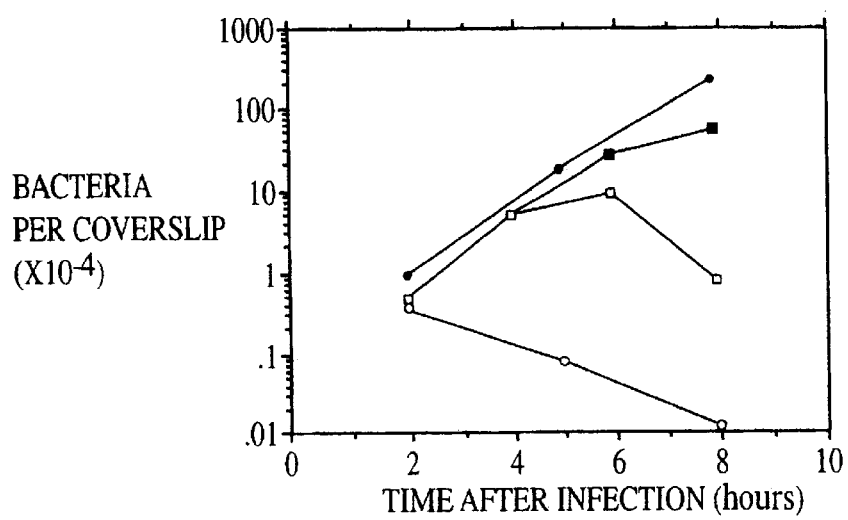
FIGS. 7A through 7C, is a series of graphs depicting infection of mammalian cells with the dal⁻dat⁻ double mutant (open circles) and wild-type strains of *L. monocytogenes* (closed circles). Mammalian cells which were infected included J744 murine macrophage-like cells (FIG. 7A), primary murine bone marrow macrophages (FIG. 7B), and human epithelial cells (HeLa) (FIG. 7C).
Figure 7B:
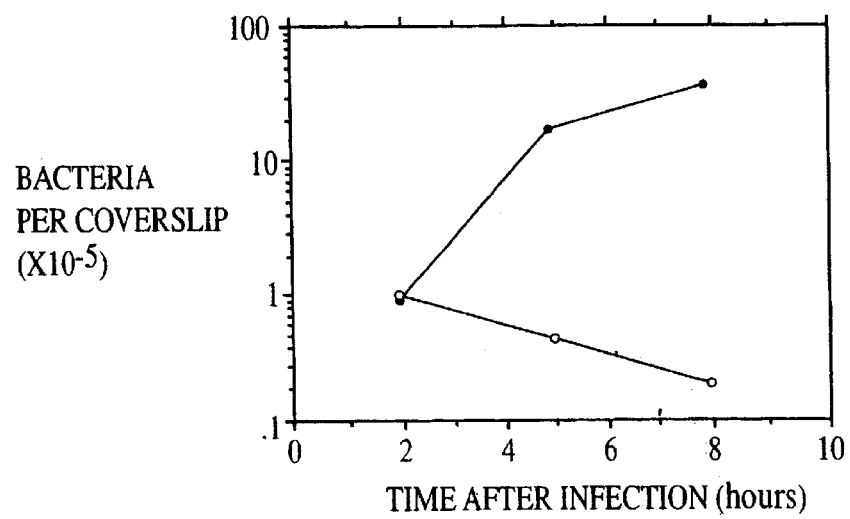
Figure 7C:
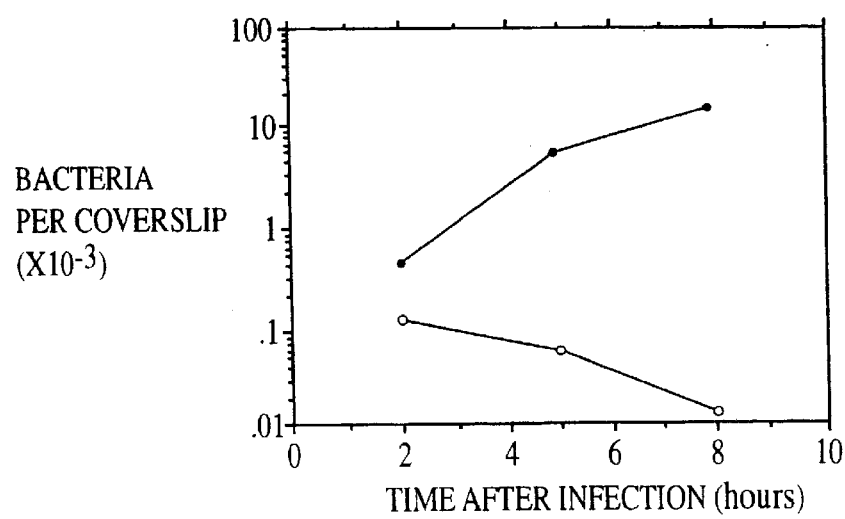

To quantify some of these observations, the number of intracellular bacteria (defined by gentamicin resistance) that could form colonies on medium containing D-alanine was enumerated at several times after infection (FIG. 7). The data clearly demonstrate that the double mutant was unable to replicate in J774 cells, and in fact slowly died during the course of the experiment. The data also illustrate that the replication-defective phenotype of the double mutant was supressed by the inclusion of D-alanine (at 100 $\mu$/ml)in the tissue culture medium at the time of infection. This suppression was reversed within 2 hours after removal of the D-alanine. The phenotype of the mutant bacteria was also examined in mouse bone marrow-derived macrophages and in the HeLa cell line of human epithelaial cells. It was determined that the double mutant was unable to replicate in either of these cell types as well (FIG. 7, Panels B and C).

It was again observed that double-mutant-infected macrophages possessed pychnotic nuclei more frequently than did macrophages infected with wild-type bacteria. Infection of bone marrow macrophages was employed to examine the intracytoplasmic status of the bacteria. Within a few hours after infection of cells by *L. monocytogenes*, when the bacteria have escaped from the phagosome, host actin filaments form a dense cloud around the intracytoplasmic bacteria, and then rearrange to form a polarized comet tail which propels the bacteria through the cytoplasm (Tilney et al., 1989, supra). The actin can readily be visualized using appropriately labeled anti-Listeria antibodies. At 2 hours post-infection using a multiplicity of infection of about 5 bacteria per cell, 25% of wild type bacteria associated with J774 macrophages were surrounded with a halo of stained actin (FIG. 8, Panel A), and at 5 hours, virtually 100% of infected cells exhibited actin staining, some cells having long actin tails (FIG. 8, Panel B). However, the staining of actin in double-mutant infected macrophages was much rarer (less than 2%) when compared with wild type infected cells. Nevertherless, if D-alanine was present during only the 30 minute period of bacterial adsorption, at 2 hours post-infection 22% of the mutant cell-associated bacteria were surrounded with actin (FIG. 8, Panel C); at 5 hours, this number of intracytoplasmic bacteria had risen to only 27% (FIG. 8, Panel D). If D-alanine was present during the entire infection period (FIG. 8, Panel E), the result observed in these cells at 5 hours was indistinguishable from those observed in wild type infected cells.

Since J774 cells have long been culture adapted and reflect very few of the normal properties of tissue macrophages, the entry of mutant bacteria into the cytosol of primary bone marrow macrophages which had been in culture for only 6 days was examined. Because these cells demonstrate the high bacterial killing capacity of normal macrophages, they were infected at a ratio of about 50 bacteria per cell. Under these conditions, at 2 hours after infection, 6.8% of the double mutant bacteria were found to be associated with actin in these cells, and this number increased to the same level as that observed after wild type infection (19%) by the inclusion of D-alanine for the first 30 minutes of the infection (18.2%) or for the entire period of infection (19.4%). Therefore, depending on the cell type examined, mutant bacteria in the absence of D-alanine either exhibited a very low or moderate efficiency of entering the host cytosol, or exhibited reduced binding of actin onto their surface. However, the brief presence of D-alanine during the initial phase of infection allowed a normal fraction of bacteria to enter the cytosol and bind actin.

Induction of an Immune Response Using the Attenuated Bacteria

Infection of mice with *L. monocytogenes* produces a long-lived state of specific immunologic memory that enables the infected host to resist lethal challenge by the same organism for months following the primary infection. To determine whether infection of mice with sub-lethal doses of the double mutant could induce this important long lasting state of immunity, the following experiments were performed.

Figure 9:
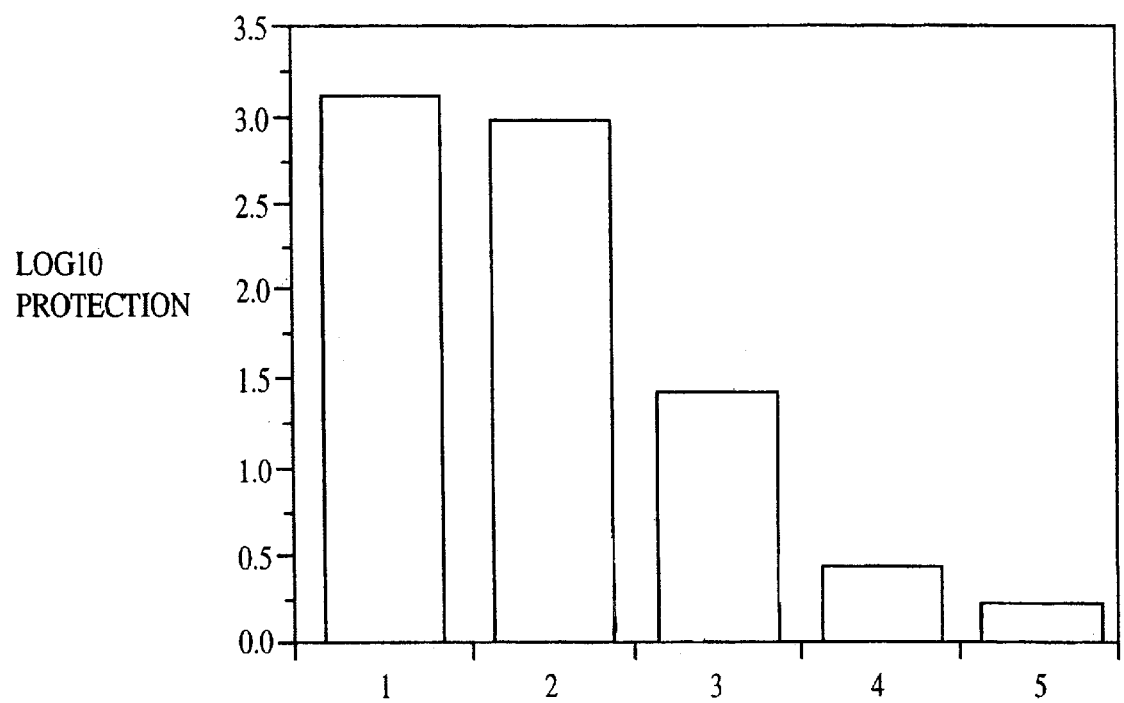
FIG. 9 is a graph depicting the protection of BALB/c mice against challenge with ten times the $LD_{50}$ of wild-type *L. monocytogenes* by immunization with the dal⁻dat⁻ double mutant strain of *L. monocytogenes*. Groups of 5 mice were immunized with the following organisms: (1) $4 \times 10^2$ wild-type *L. monocytogenes*, (2) $2 \times 10^7$ dal⁻dat⁻ (+D-alanine supplement), (3) $2 \times 10^5$ dal⁻dat⁻ (+D-alanine supplement), (4) $2 \times 10^4$ dal⁻dat⁻ (+D-alanine supplement), (5) $2 \times 10^2$ dal⁻dat⁻ mutant dal⁻dat⁻ (no D-alanine supplement). Mice were challenged 21–28 days after immunization. $Log_{10}$ protection was calculated as described in the Examples.

Mice were injected intravenously with $2 \times 10^7$ ($<0.05$ $LD_{50}$) of the double mutant and were challenged 3 to 4 weeks later with 10 $LD_{50}$ of wild type *L. monocytogenes*. D-alanine (20 mg) was provided in the initial inoculum of mutant organisms to be certain that the organisms were fully viable at the time of initial infection (this had the effect of reducing the $LD_{50}$ about 10 fold). The data presented in FIG. 9 demonstrate that the level of antilisterial protection was approximately 3 $\log_{10}$ following a single infection by the mutant bacteria, a similar level of protection to that generated by immunization with the wild-type organism. The same dose of mutant bacteria injected without D-alanine provided little protection.

Figure 10:
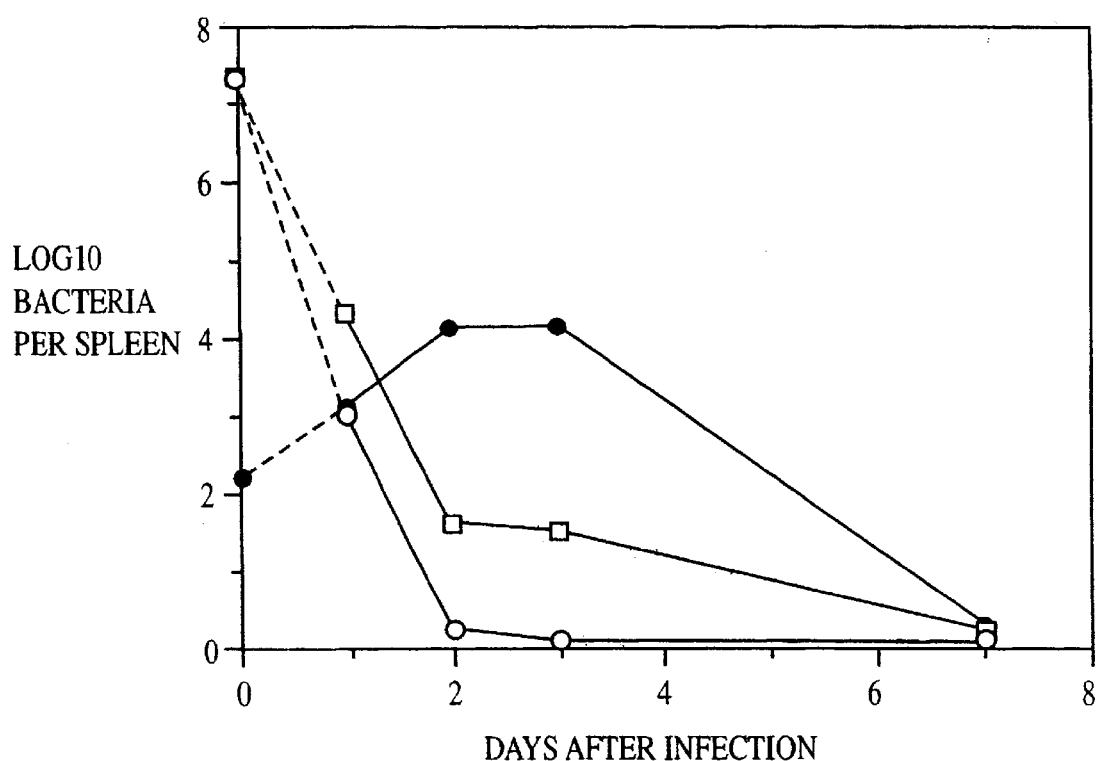
FIG. 10 is a graph depicting the recovery of bacteria from spleens of BALB/c mice following sublethal infection with wild type *L. monocytogenes* (closed circles), the dal⁻dat⁻ mutant in the absence of D-alanine (open circles), and the dal⁻ dat⁻ mutant in the presence of 20 mg D-alanine (open squares). The points at day 0 illustrate the total number of organisms injected, not the number of bacteria per spleen.

To determine whether the high degree of protection generated by the mutant bacteria could be accounted by their survival and replication in the infected mice, the spleens of infected animals were removed and the number of surviving mutant bacteria was assessed. In FIG. 10 there is shown evidence which indicates that in the absence of D-alanine, few mutant organisms survived for more than one day after infection; the presence of D-alanine in the initial inoculum permitted a few bacteria to survive longer. Importantly, the almost complete protection obtained using mutant bacteria occurred in spite of the fact that by 2 days post-infection more than 100-fold fewer bacteria were detected in the spleens of mutant infected mice compared with wild type infected animals.

Figure 11A:
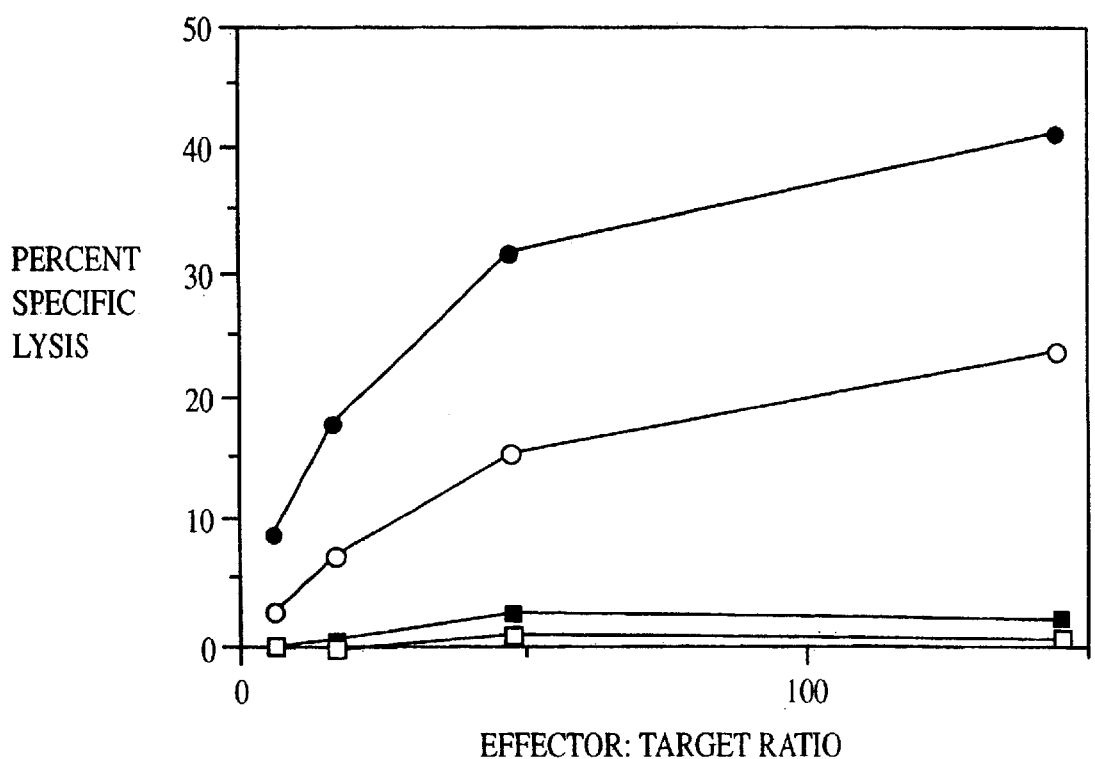
FIGS. 11A and 11B, is a series of graphs depicting the cytolytic activity of splenocytes isolated from mice at 10–14 days after infection with in FIG. 11A, wild type *L. monocytogenes* (●○), or niave control (■□).
Figure 11B:
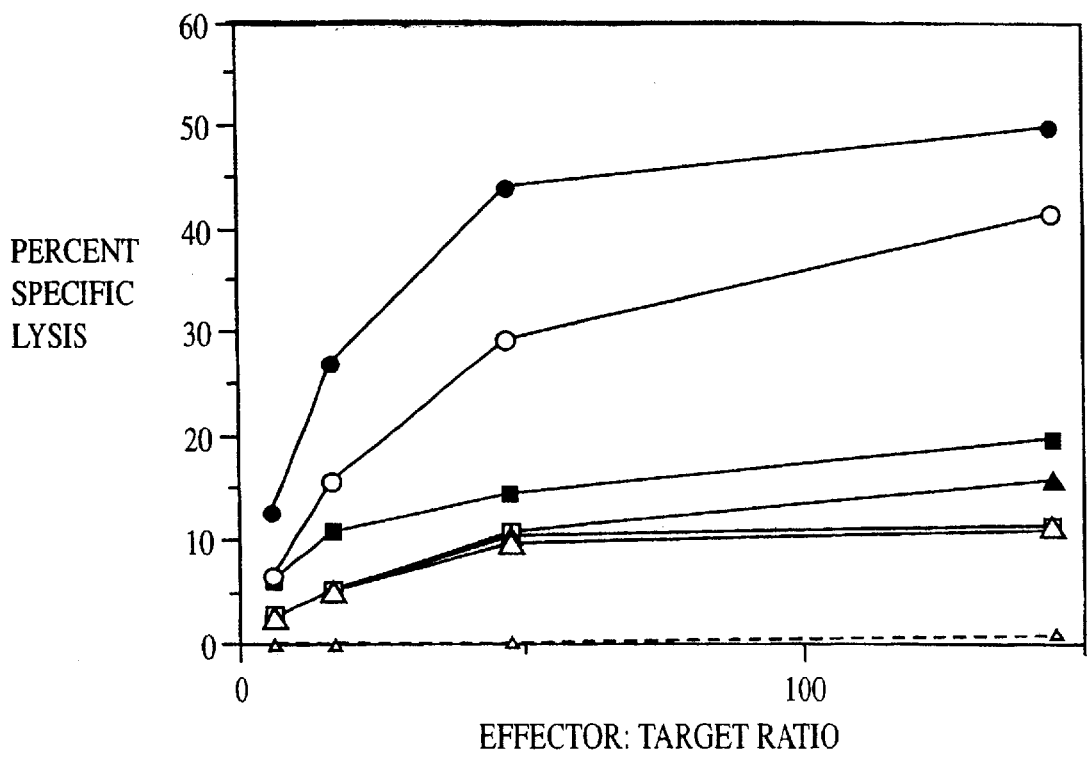

Listerolysin O peptide 91–99 is the major epitope of the listerolysin O protein and one of the major epitopes to which mice respond when mounting a cell mediated immune response against infection with *L. monocytogenes* (Bouwer et al., 1996, Infect. Immun. 64:2515–2522; Harty et al., 1992, J. Exp. Med. 175:1531–1538; Pamer et al., 1991, Nature 353:852–855). To determine whether the protective immunity generated by infection with the dal⁻dat⁻ double mutant strain of *L. monocytogenes* was associated with the induction of cytolytic T cells, splenocytes obtained from infected animals were assayed for their ability to lyse target cells loaded with this peptide. In FIG. 11 there is shown the fact that animals that were infected intraperitoneally with $3 \times 10^7$ and were provided D-alanine subcutaneously both before and after infection exhibited strong CTL responses directed against the LLO peptide. Likewise, mice provided with D-alanine in their drinking water before and after infection mounted a modest CTL response after single infection with $3 \times 10^7$ mutant bacteria. In the absence of D-alanine, animals infected with and boosted one time with $3 \times 10^7$ bacteria, also exhibited a modest CTL response to LLO peptide 91–99. Single infection with $3 \times 10^7$ of the double mutant bacteria in the absence of D-alanine produced no significant response (FIG. 11).

The disclosures of each and every publication, patent, and patent application cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. An isolated polynucleotide that is at least 90% identical to the polynucleotide sequence set forth in SEQ ID NO:1, wherein the polypeptide encoded by said isolated polynucleotide has dal activity.

* * * * *

SEQUENCE LISTING

<160> NUMBER OF SEQ ID NOS: 9

<210> SEQ ID NO 1
<211> LENGTH: 1107
<212> TYPE: DNA
<213> ORGANISM: Listeria monocytogenes

<400> SEQUENCE: 1

```
atggtgacag gctggcatcg tccaacatgg attgaaatag accgcgcagc aattcgcgaa      60
aatataaaaa atgaacaaaa taaactcccg gaaagtgtcg acttatgggc agtagtcaaa     120
gctaatgcat atggtcacgg aattatcgaa gttgctagga cggcgaaaga agctggagca     180
aaaggtttct gcgtagccat tttagatgag gcactggctc ttagagaagc tggatttcaa     240
gatgacttta ttcttgtgct tggtgcaacc agaaaagaag atgctaatct ggcagccaaa     300
aaccacattt cacttactgt ttttagagaa gattggctag agaatctaac gctagaagca     360
acacttcgaa ttcatttaaa agtagatagc ggtatggggc gtctcggtat tcgtacgact     420
```

```
gaagaagcac ggcgaattga agcaaccagt actaatgatc accaattaca actggaaggt      480
atttacacgc attttgcaac agccgaccag ctagaaacta gttattttga acaacaatta      540
gctaagttcc aaacgatttt aacgagttta aaaaaacgac caacttatgt tcatacagcc      600
aattcagctg cttcattgtt acagccacaa atcgggtttg atgcgattcg ctttggtatt      660
tcgatgtatg gattaactcc ctccacagaa atcaaaacta gcttgccgtt tgagcttaaa      720
cctgcacttg cactctatac cgagatggtt catgtgaaag aacttgcacc aggcgatagc      780
gttagctacg gagcaactta tacagcaaca gagcgagaat gggttgcgac attaccaatt      840
ggctatgcgg atggattgat tcgtcattac agtggtttcc atgtttagt agacggtgaa       900 ccagctccaa tcattggtcg agtttgtatg gatcaaacca tcataaaact accacgtgaa      960
tttcaaactg gttcaaaagt aacgataatt ggcaaagatc atggtaacac ggtaacagca     1020
gatgatgccg ctcaatattt agatacaatt aattatgagg taacttgttt gttaaatgag     1080
cgcataccta gaaatacat ccattag                                          1107
```

<210> SEQ ID NO 2
<211> LENGTH: 368
<212> TYPE: PRT
<213> ORGANISM: Listeria monocytogenes

<400> SEQUENCE: 2

```
Met Val Thr Gly Trp His Arg Pro Thr Trp Ile Glu Ile Asp Arg Ala
 1               5                  10                  15

Ala Ile Arg Glu Asn Ile Lys Asn Glu Gln Asn Lys Leu Pro Glu Ser
             20                  25                  30

Val Asp Leu Trp Ala Val Val Lys Ala Asn Ala Tyr Gly His Gly Ile
         35                  40                  45

Ile Glu Val Ala Arg Thr Ala Lys Glu Ala Gly Ala Lys Gly Phe Cys
     50                  55                  60

Val Ala Ile Leu Asp Glu Ala Leu Ala Leu Arg Glu Ala Gly Phe Gln
 65                  70                  75                  80

Asp Asp Phe Ile Leu Val Leu Gly Ala Thr Arg Lys Glu Asp Ala Asn
                 85                  90                  95

Leu Ala Ala Lys Asn His Ile Ser Leu Thr Val Phe Arg Glu Asp Trp
            100                 105                 110

Leu Glu Asn Leu Thr Leu Glu Ala Thr Leu Arg Ile His Leu Lys Val
        115                 120                 125

Asp Ser Gly Met Gly Arg Leu Gly Ile Arg Thr Thr Glu Glu Ala Arg
    130                 135                 140

Arg Ile Glu Ala Thr Ser Thr Asn Asp His Gln Leu Gln Leu Glu Gly
145                 150                 155                 160

Ile Tyr Thr His Phe Ala Thr Ala Asp Gln Leu Glu Thr Ser Tyr Phe
                165                 170                 175

Glu Gln Gln Leu Ala Lys Phe Gln Thr Ile Leu Thr Ser Leu Lys Lys
            180                 185                 190

Arg Pro Thr Tyr Val His Thr Ala Asn Ser Ala Ala Ser Leu Leu Gln
        195                 200                 205

Pro Gln Ile Gly Phe Asp Ala Ile Arg Phe Gly Ile Ser Met Tyr Gly
    210                 215                 220

Leu Thr Pro Ser Thr Glu Ile Lys Thr Ser Leu Pro Phe Glu Leu Lys
225                 230                 235                 240

Pro Ala Leu Ala Leu Tyr Thr Glu Met Val His Val Lys Glu Leu Ala
```

```
                        245                 250                 255
Pro Gly Asp Ser Val Ser Tyr Gly Ala Thr Tyr Thr Ala Thr Glu Arg
                260                 265                 270
Glu Trp Val Ala Thr Leu Pro Ile Gly Tyr Ala Asp Gly Leu Ile Arg
            275                 280                 285
His Tyr Ser Gly Phe His Val Leu Val Asp Gly Glu Pro Ala Pro Ile
        290                 295                 300
Ile Gly Arg Val Cys Met Asp Gln Thr Ile Ile Lys Leu Pro Arg Glu
305                 310                 315                 320
Phe Gln Thr Gly Ser Lys Val Thr Ile Ile Gly Lys Asp His Gly Asn
                325                 330                 335
Thr Val Thr Ala Asp Asp Ala Ala Gln Tyr Leu Asp Thr Ile Asn Tyr
                340                 345                 350
Glu Val Thr Cys Leu Leu Asn Glu Arg Ile Pro Arg Lys Tyr Ile His
            355                 360                 365

<210> SEQ ID NO 3
<211> LENGTH: 386
<212> TYPE: PRT
<213> ORGANISM: Listeria monocytogenes

<400> SEQUENCE: 3

Met Asn Asp Phe His Arg Asp Thr Trp Ala Glu Val Asp Leu Asp Ala
 1               5                  10                  15
Ile Tyr Asp Asn Val Glu Asn Leu Arg Arg Leu Leu Pro Asp Asp Thr
                20                  25                  30
His Ile Met Ala Val Val Lys Ala Asn Ala Tyr Gly His Gly Asp Val
            35                  40                  45
Gln Val Ala Arg Thr Ala Leu Glu Arg Gly Pro Pro Pro Ala Val Ala
        50                  55                  60
Phe Leu Asp Glu Ala Leu Ala Leu Arg Glu Lys Gly Ile Glu Ala Pro
65                  70                  75                  80
Ile Leu Val Leu Gly Ala Ser Arg Pro Ala Asp Ala Ala Leu Ala Ala
                85                  90                  95
Gln Gln Arg Ile Ala Leu Thr Val Phe Arg Ser Asp Trp Leu Glu Glu
            100                 105                 110
Ala Ser Ala Leu Tyr Ser Gly Pro Phe Pro Ile His Phe His Leu Lys
        115                 120                 125
Met Asp Thr Gly Met Gly Arg Leu Gly Val Lys Asp Glu Glu Glu Thr
    130                 135                 140
Lys Arg Ile Val Ala Leu Ile Glu Arg His Pro His Phe Val Leu Glu
145                 150                 155                 160
Gly Leu Tyr Thr His Phe Ala Thr Ala Asp Glu Val Asn Thr Asp Tyr
                165                 170                 175
Phe Ser Tyr Gln Tyr Thr Arg Phe Leu His Met Leu Glu Trp Leu Pro
            180                 185                 190
Ser Arg Pro Pro Leu Val His Cys Ala Asn Ser Ala Ala Ser Leu Arg
        195                 200                 205
Phe Pro Asp Arg Thr Phe Asn Met Val Arg Phe Gly Ile Ala Met Tyr
    210                 215                 220
Gly Leu Ala Pro Ser Pro Gly Ile Lys Pro Leu Leu Pro Tyr Pro Leu
225                 230                 235                 240
Lys Glu Ala Phe Ser Leu His Ser Arg Leu Val His Val Lys Lys Leu
                245                 250                 255
```

```
Gln Pro Gly Glu Lys Val Ser Tyr Gly Ala Thr Tyr Thr Ala Gln Thr
                260                 265                 270

Glu Glu Trp Ile Gly Thr Ile Pro Ile Gly Tyr Ala Asp Gly Val Arg
            275                 280                 285

Arg Leu Gln His Phe His Val Leu Val Asp Gly Gln Lys Ala Pro Ile
        290                 295                 300

Val Gly Arg Ile Cys Met Asp Gln Cys Met Ile Arg Leu Pro Gly Pro
305                 310                 315                 320

Leu Pro Val Gly Thr Lys Val Thr Leu Ile Gly Arg Gln Gly Asp Glu
                325                 330                 335

Val Ile Ser Ile Asp Asp Val Ala Arg His Leu Glu Thr Ile Asn Tyr
            340                 345                 350

Glu Val Pro Cys Thr Ile Ser Tyr Arg Val Pro Arg Ile Phe Phe Arg
        355                 360                 365

His Lys Arg Ile Met Glu Val Arg Asn Ala Ile Gly Arg Gly Glu Ser
    370                 375                 380

Ser Ala
385

<210> SEQ ID NO 4
<211> LENGTH: 389
<212> TYPE: PRT
<213> ORGANISM: Listeria monocytogenes

<400> SEQUENCE: 4

Met Ser Thr Lys Pro Phe Tyr Arg Asp Thr Trp Ala Glu Ile Asp Leu
  1               5                  10                  15

Ser Ala Ile Lys Glu Asn Val Ser Asn Met Lys Lys His Ile Gly Glu
                20                  25                  30

His Val His Leu Met Ala Val Glu Lys Ala Asn Ala Tyr Gly His Gly
            35                  40                  45

Asp Ala Glu Thr Ala Lys Ala Leu Asp Ala Gly Ala Ser Cys Leu
    50                  55                  60

Ala Met Ala Ile Leu Asp Glu Ala Ile Ser Leu Arg Lys Lys Gly Leu
 65                  70                  75                  80

Lys Ala Pro Ile Leu Val Leu Gly Ala Val Pro Pro Glu Tyr Val Ala
                 85                  90                  95

Ile Ala Ala Glu Tyr Asp Val Thr Leu Thr Gly Tyr Ser Val Glu Trp
            100                 105                 110

Leu Gln Glu Ala Ala Arg His Thr Lys Lys Gly Ser Leu His Phe His
        115                 120                 125

Leu Lys Val Asp Thr Gly Met Asn Arg Leu Gly Val Lys Thr Glu Glu
    130                 135                 140

Glu Val Gln Asn Val Met Ala Ile Leu Asp Arg Asn Pro Arg Leu Lys
145                 150                 155                 160

Cys Lys Gly Val Phe Thr His Phe Ala Thr Ala Asp Glu Lys Glu Arg
                165                 170                 175

Gly Tyr Phe Leu Met Gln Phe Glu Arg Phe Lys Glu Leu Ile Ala Pro
            180                 185                 190

Leu Pro Leu Lys Asn Leu Met Val His Cys Ala Asn Ser Ala Ala Gly
        195                 200                 205

Leu Arg Leu Lys Lys Gly Phe Phe Asn Ala Val Arg Phe Gly Ile Gly
    210                 215                 220

Met Tyr Gly Leu Arg Pro Ser Ala Asp Met Ser Asp Glu Ile Pro Phe
225                 230                 235                 240
```

Gln Leu Arg Pro Ala Phe Thr Leu His Ser Thr Leu Ser His Val Lys
                245                 250                 255

Leu Ile Arg Lys Gly Glu Ser Val Ser Tyr Gly Ala Glu Tyr Thr Ala
            260                 265                 270

Glu Lys Asp Thr Trp Ile Gly Thr Val Pro Val Gly Tyr Ala Asp Gly
        275                 280                 285

Trp Leu Arg Lys Leu Lys Gly Thr Asp Ile Leu Val Lys Gly Lys Arg
    290                 295                 300

Leu Lys Ile Ala Gly Arg Ile Cys Met Asp Gln Phe Met Val Glu Leu
305                 310                 315                 320

Asp Gln Glu Tyr Pro Pro Gly Thr Lys Val Thr Leu Ile Gly Arg Gln
                325                 330                 335

Gly Asp Glu Tyr Ile Ser Met Asp Glu Ile Ala Gly Arg Leu Glu Thr
            340                 345                 350

Ile Asn Tyr Glu Val Ala Cys Thr Ile Ser Ser Arg Val Pro Arg Met
        355                 360                 365

Phe Leu Glu Asn Gly Ser Ile Met Glu Val Arg Asn Pro Leu Leu Gln
    370                 375                 380

Val Asn Ile Ser Asn
385

<210> SEQ ID NO 5
<211> LENGTH: 870
<212> TYPE: DNA
<213> ORGANISM: Listeria monocytogenes

<400> SEQUENCE: 5
atgaaagtat tagtaaataa ccatttagtt gaaagagaag atgccacagt tgacattgaa      60
gaccgcggat atcagtttgg tgatggtgta tatgaagtag ttcgtctata taatggaaaa     120
ttctttactt ataatgaaca cattgatcgc ttatatgcta gtgcagcaaa aattgactta     180
gttattcctt attccaaaga agagctacgt gaattacttg aaaaattagt tgccgaaaat     240
aatatcaata cagggaatgt ctatttacaa gtgactcgtg gtgttcaaaa cccacgtaat     300
catgtaatcc ctgatgattt ccctctagaa ggcgttttaa cagcagcagc tcgtgaagta     360
cctagaaacg agcgtcaatt cgttgaaggt ggaacggcga ttacagaaga agatgtgcgc     420
tggttacgct gtgatattaa gagcttaaac cttttaggaa atattctagc aaaaaataaa     480
gcacatcaac aaaatgcttt ggaagctatt ttacatcgcg gggaacaagt aacagaatgt     540
tctgcttcaa acgtttctat tattaaagat ggtgtattat ggacgcatgc ggcagataac     600
ttaatcttaa atggtatcac tcgtcaagtt atcattgatg ttgcgaaaaa gaatggcatt     660
cctgttaaag aagcggattt cactttaaca gaccttcgtg aagcggatga agtgttcatt     720
tcaagtacaa ctattgaaat tacacctatt acgcatattg acggagttca gtagctgac      780 ggaaaacgtg gaccaattac agcgcaactt catcaatatt ttgtagaaga aatcactcgt     840
gcatgtggcg aattagagtt tgcaaaataa                                      870

<210> SEQ ID NO 6
<211> LENGTH: 289
<212> TYPE: PRT
<213> ORGANISM: Listeria monocytogenes

<400> SEQUENCE: 6

Met Lys Val Leu Val Asn Asn His Leu Val Glu Arg Glu Asp Ala Thr
1               5                   10                  15

```
Val Asp Ile Glu Asp Arg Gly Tyr Gln Phe Gly Asp Gly Val Tyr Glu
            20                  25                  30

Val Val Arg Leu Tyr Asn Gly Lys Phe Phe Thr Tyr Asn Glu His Ile
        35                  40                  45

Asp Arg Leu Tyr Ala Ser Ala Ala Lys Ile Asp Leu Val Ile Pro Tyr
    50                  55                  60

Ser Lys Glu Glu Leu Arg Glu Leu Leu Glu Lys Leu Val Ala Glu Asn
65                  70                  75                  80

Asn Ile Asn Thr Gly Asn Val Tyr Leu Gln Val Thr Arg Gly Val Gln
                85                  90                  95

Asn Pro Arg Asn His Val Ile Pro Asp Asp Phe Pro Leu Glu Gly Val
            100                 105                 110

Leu Thr Ala Ala Ala Arg Glu Val Pro Arg Asn Glu Arg Gln Phe Val
        115                 120                 125

Glu Gly Gly Thr Ala Ile Thr Glu Glu Asp Val Arg Trp Leu Arg Cys
    130                 135                 140

Asp Ile Lys Ser Leu Asn Leu Leu Gly Asn Ile Leu Ala Lys Asn Lys
145                 150                 155                 160

Ala His Gln Gln Asn Ala Leu Glu Ala Ile Leu His Arg Gly Glu Gln
                165                 170                 175

Val Thr Glu Cys Ser Ala Ser Asn Val Ser Ile Ile Lys Asp Gly Val
            180                 185                 190

Leu Trp Thr His Ala Ala Asp Asn Leu Ile Leu Asn Gly Ile Thr Arg
        195                 200                 205

Gln Val Ile Ile Asp Val Ala Lys Lys Asn Gly Ile Pro Val Lys Glu
    210                 215                 220

Ala Asp Phe Thr Leu Thr Asp Leu Arg Glu Ala Asp Glu Val Phe Ile
225                 230                 235                 240

Ser Ser Thr Thr Ile Glu Ile Thr Pro Ile Thr His Ile Asp Gly Val
                245                 250                 255

Gln Val Ala Asp Gly Lys Arg Gly Pro Ile Thr Ala Gln Leu His Gln
            260                 265                 270

Tyr Phe Val Glu Glu Ile Thr Arg Ala Cys Gly Glu Leu Glu Phe Ala
        275                 280                 285

Lys

<210> SEQ ID NO 7
<211> LENGTH: 282
<212> TYPE: PRT
<213> ORGANISM: Listeria monocytogenes

<400> SEQUENCE: 7

Met Thr Lys Val Phe Ile Asn Gly Glu Phe Ile Asp Gln Asn Glu Ala
1               5                   10                  15

Lys Val Ser Tyr Glu Asp Arg Gly Tyr Val Phe Gly Asp Gly Ile Tyr
            20                  25                  30

Glu Tyr Ile Arg Ala Tyr Asp Gly Lys Leu Phe Thr Val Thr Glu His
        35                  40                  45

Phe Glu Arg Phe Ile Arg Ser Ala Ser Glu Ile Gln Leu Asp Leu Gly
    50                  55                  60

Tyr Thr Val Glu Glu Leu Ile Asp Val Val Arg Glu Leu Leu Lys Val
65                  70                  75                  80

Asn Asn Ile Gln Asn Gly Gly Ile Tyr Ile Gln Ala Thr Arg Gly Val
                85                  90                  95
```

```
Ala Pro Arg Asn His Ser Phe Pro Thr Pro Glu Val Lys Pro Val Ile
            100                 105                 110

Met Ala Phe Ala Lys Ser Tyr Asp Arg Pro Tyr Asp Asp Leu Glu Asn
            115                 120                 125

Gly Ile Asn Ala Ala Thr Val Glu Asp Ile Arg Trp Leu Arg Cys Asp
        130                 135                 140

Ile Lys Ser Leu Asn Leu Leu Gly Asn Val Leu Ala Lys Glu Tyr Ala
145                 150                 155                 160

Val Lys Tyr Asn Ala Gly Glu Ala Ile Gln His Arg Gly Glu Thr Val
                165                 170                 175

Thr Glu Gly Ala Ser Ser Asn Val Tyr Ala Ile Lys Asp Gly Ala Ile
            180                 185                 190

Tyr Thr His Pro Val Asn Asn Tyr Ile Leu Asn Gly Ile Thr Arg Lys
        195                 200                 205

Val Ile Lys Trp Ile Ser Glu Asp Glu Asp Ile Pro Phe Lys Glu Glu
        210                 215                 220

Thr Phe Thr Val Glu Phe Leu Lys Asn Ala Asp Glu Val Ile Val Ser
225                 230                 235                 240

Ser Thr Ser Ala Glu Val Thr Pro Val Val Lys Ile Asp Gly Glu Gln
                245                 250                 255

Val Gly Asp Gly Lys Val Gly Pro Val Thr Arg Gln Leu Gln Glu Gly
            260                 265                 270

Phe Asn Lys Tyr Ile Glu Ser Arg Ser Ser
            275                 280

<210> SEQ ID NO 8
<211> LENGTH: 283
<212> TYPE: PRT
<213> ORGANISM: Listeria monocytogenes

<400> SEQUENCE: 8

Met Ala Tyr Ser Leu Trp Asn Asp Gln Ile Val Glu Glu Gly Ser Ile
1               5                   10                  15

Thr Ile Ser Pro Glu Asp Arg Gly Tyr Gln Phe Gly Asp Gly Ile Tyr
            20                  25                  30

Glu Val Ile Lys Val Tyr Asn Gly His Met Phe Thr Ala Gln Glu His
        35                  40                  45

Ile Asp Arg Phe Tyr Ala Ser Ala Glu Lys Ile Arg Leu Val Ile Pro
    50                  55                  60

Tyr Thr Lys Asp Val Leu His Lys Leu Leu His Asp Leu Ile Glu Lys
65                  70                  75                  80

Asn Asn Leu Asn Thr Gly His Val Tyr Phe Gln Ile Thr Arg Gly Thr
                85                  90                  95

Thr Ser Arg Asn His Ile Phe Pro Asp Ala Ser Val Pro Ala Val Leu
            100                 105                 110

Thr Gly Asn Val Lys Thr Gly Glu Arg Ser Ile Glu Asn Phe Glu Lys
            115                 120                 125

Gly Val Lys Ala Thr Leu Val Glu Asp Val Arg Trp Leu Arg Cys Asp
        130                 135                 140

Ile Lys Ser Leu Asn Leu Leu Gly Ala Val Leu Ala Lys Gln Glu Ala
145                 150                 155                 160

Ser Glu Lys Gly Cys Tyr Glu Ala Ile Leu His Arg Gly Asp Ile Ile
                165                 170                 175

Thr Glu Cys Ser Ser Ala Asn Val Tyr Gly Ile Lys Asp Gly Lys Leu
```

-continued

```
                        180                 185                 190
Tyr Thr His Pro Ala Asn Asn Tyr Ile Leu Asn Gly Ile Thr Arg Gln
            195                 200                 205

Val Ile Leu Lys Cys Ala Ala Glu Ile Asn Leu Pro Val Ile Glu Glu
    210                 215                 220

Pro Met Thr Lys Gly Asp Leu Leu Thr Met Asp Glu Ile Ile Val Ser
225                 230                 235                 240

Ser Val Ser Ser Glu Val Thr Pro Val Ile Asp Val Asp Gly Gln Gln
            245                 250                 255

Ile Gly Ala Gly Val Pro Gly Glu Trp Thr Arg Lys Leu Gln Lys Ala
            260                 265                 270

Phe Glu Ala Lys Leu Pro Ile Ser Ile Asn Ala
            275                 280

<210> SEQ ID NO 9
<211> LENGTH: 283
<212> TYPE: PRT
<213> ORGANISM: Listeria monocytogenes

<400> SEQUENCE: 9

Met Gly Tyr Thr Leu Trp Asn Asp Gln Ile Val Lys Asp Glu Glu Val
1               5                   10                  15

Lys Ile Asp Lys Glu Asp Arg Gly Tyr Gln Phe Gly Asp Gly Val Tyr
            20                  25                  30

Glu Val Val Lys Val Tyr Asn Gly Glu Met Phe Thr Val Asn Glu His
        35                  40                  45

Ile Asp Arg Leu Tyr Ala Ser Ala Glu Lys Ile Arg Ile Thr Ile Pro
    50                  55                  60

Tyr Thr Lys Asp Lys Phe His Gln Leu Leu His Glu Leu Val Glu Lys
65                  70                  75                  80

Asn Glu Leu Asn Thr Gly His Ile Tyr Phe Gln Val Thr Arg Gly Thr
                85                  90                  95

Ser Pro Arg Ala His Gln Phe Pro Glu Asn Thr Val Lys Pro Val Ile
            100                 105                 110

Ile Gly Tyr Thr Lys Glu Asn Pro Arg Pro Leu Glu Asn Leu Glu Lys
        115                 120                 125

Gly Val Lys Ala Thr Phe Val Glu Asp Ile Arg Trp Leu Arg Cys Asp
    130                 135                 140

Ile Lys Ser Leu Asn Leu Leu Gly Ala Val Leu Ala Lys Gln Glu Ala
145                 150                 155                 160

His Glu Lys Gly Cys Tyr Glu Ala Ile Leu His Arg Asn Asn Thr Val
                165                 170                 175

Thr Glu Gly Ser Ser Asn Val Phe Gly Ile Lys Asp Gly Ile Leu
            180                 185                 190

Tyr Thr His Pro Ala Asn Asn Met Ile Leu Lys Gly Ile Thr Arg Asp
            195                 200                 205

Val Val Ile Ala Cys Ala Asn Glu Ile Asn Met Pro Val Lys Glu Ile
    210                 215                 220

Pro Phe Thr Thr His Glu Ala Leu Lys Met Asp Glu Leu Phe Val Thr
225                 230                 235                 240

Ser Thr Thr Ser Glu Ile Thr Pro Val Ile Glu Ile Asp Gly Lys Leu
            245                 250                 255
```

```
Ile Arg Asp Gly Lys Val Gly Glu Trp Thr Arg Lys Leu Gln Lys Gln
            260                 265                 270

Phe Glu Thr Lys Ile Pro Lys Pro Leu His Ile
            275                 280
```